United States Patent
Jørgensen et al.

(10) Patent No.: US 12,398,106 B2
(45) Date of Patent: Aug. 26, 2025

(54) CATECHOLAMINE CARBAMATE PRODRUGS FOR USE IN THE TREATMENT OF PARKINSON'S DISEASE

(71) Applicant: H. Lundbeck A/S, Valby (DK)

(72) Inventors: Morten Jørgensen, Valby (DK); Erhad Ascic, Valby (DK); Karin Sjödin, Valby (DK); Klaus Gjervig Jensen, Valby (DK); Jarkko Tapani Rautio, Valby (DK)

(73) Assignee: H. Lundbeck A/S, Valby (DK)

( * ) Notice: Subject to any disclaimer, the term of this patent is extended or adjusted under 35 U.S.C. 154(b) by 930 days.

(21) Appl. No.: 17/606,332

(22) PCT Filed: May 19, 2020

(86) PCT No.: PCT/EP2020/063918
§ 371 (c)(1),
(2) Date: Oct. 25, 2021

(87) PCT Pub. No.: WO2020/234277
PCT Pub. Date: Nov. 26, 2020

(65) Prior Publication Data
US 2022/0213040 A1   Jul. 7, 2022

(30) Foreign Application Priority Data

May 21, 2019 (DK) .............................. PA201900606
May 24, 2019 (DK) .............................. PA201900631

(51) Int. Cl.
*C07D 215/14* (2006.01)

(52) U.S. Cl.
CPC .................................. *C07D 215/14* (2013.01)

(58) Field of Classification Search
CPC .................................................. C07D 215/14
See application file for complete search history.

(56) References Cited

U.S. PATENT DOCUMENTS

| | | |
|---|---|---|
| 3,132,171 A | 5/1964 | Plaut |
| 4,374,829 A | 2/1983 | Harris |
| 4,543,256 A | 9/1985 | Neumeyer |
| 4,565,818 A | 1/1986 | Nordmann et al. |
| 4,692,453 A | 9/1987 | Seiler |
| 5,073,547 A | 12/1991 | Casagrande et al. |
| 5,747,513 A | 5/1998 | Montanari et al. |
| 5,885,988 A | 3/1999 | Neumann et al. |
| 5,955,468 A | 9/1999 | Markstein |
| 6,410,664 B1 | 6/2002 | Bansleben et al. |
| 8,129,530 B2 | 3/2012 | Jorgensen et al. |
| 10,729,710 B2 | 8/2020 | Jensen et al. |
| 11,104,697 B2 | 8/2021 | Juhl et al. |
| 11,110,110 B2 | 9/2021 | Jensen et al. |
| 11,111,263 B2 | 9/2021 | Juhl et al. |
| 11,130,775 B2 | 9/2021 | Jensen et al. |
| 11,168,056 B2 | 11/2021 | Jacobsen et al. |
| 11,707,476 B2 | 7/2023 | Jensen et al. |
| 11,827,665 B2 | 11/2023 | Juhl et al. |
| 11,851,456 B2 | 12/2023 | Juhl et al. |
| 11,858,954 B2 | 1/2024 | Jensen et al. |
| 11,866,410 B2 | 1/2024 | Jacobsen et al. |
| 12,226,428 B2 | 2/2025 | Jensen et al. |
| 2009/0062324 A1 | 3/2009 | Jorgensen et al. |
| 2009/0124651 A1 | 5/2009 | Jorgensen et al. |
| 2012/0077836 A1 | 3/2012 | Wilkstrom et al. |
| 2017/0335357 A1 | 11/2017 | Divi et al. |
| 2020/0338102 A1 | 10/2020 | Jensen et al. |
| 2020/0369615 A1 | 11/2020 | Jacobsen et al. |
| 2020/0369705 A1 | 11/2020 | Juhl et al. |
| 2020/0369706 A1 | 11/2020 | Juhl et al. |
| 2020/0392176 A1 | 12/2020 | Jensen et al. |
| 2022/0024875 A1 | 1/2022 | Jacobsen et al. |
| 2022/0024962 A1 | 1/2022 | Jensen et al. |
| 2022/0185839 A1 | 6/2022 | Juhl et al. |
| 2022/0194978 A1 | 6/2022 | Juhl et al. |
| 2022/0213071 A1 | 7/2022 | Jorgensen et al. |
| 2022/0213136 A1 | 7/2022 | Jorgensen et al. |
| 2022/0220077 A1 | 7/2022 | Jorgensen et al. |
| 2022/0257623 A1 | 8/2022 | Jensen et al. |
| 2024/0018107 A1 | 1/2024 | Jacobsen et al. |
| 2024/0025857 A1 | 1/2024 | Jørgensen et al. |
| 2024/0156851 A1 | 5/2024 | Jensen et al. |
| 2024/0190909 A1 | 6/2024 | Jensen et al. |

(Continued)

FOREIGN PATENT DOCUMENTS

| | | |
|---|---|---|
| CN | 102746351 A | 10/2012 |
| CN | 105218606 A | 1/2016 |
| EP | 0 352 815 A1 | 1/1990 |

(Continued)

OTHER PUBLICATIONS

International Search Report and Written Opinion for Application No. PCT/EP2020/063914 mailed Jul. 14, 2020.
International Search Report and Written Opinion for Application No. PCT/EP2018/082361 mailed Feb. 22, 2019.
International Search Report and Written Opinion for Application No. PCT/EP2020/063909 mailed Jul. 2, 2020.
International Search Report and Written Opinion for Application No. PCT/EP2020/063910 mailed Jul. 14, 2020.
International Search Report and Written Opinion for Application No. PCT/EP2020/063913 mailed Jul. 15, 2020.
International Search Report and Written Opinion for Application No. PCT/EP2020/063908 mailed Sep. 11, 2020.

(Continued)

*Primary Examiner* — Timothy R Rozof
(74) *Attorney, Agent, or Firm* — Wolf, Greenfield & Sacks, P.C.

(57) ABSTRACT

The present invention provides compounds of formula (Id) that are prodrugs of catecholamine for use in treatment of neurodegenerative diseases and disorders. The present invention also provides pharmaceutical compositions comprising compounds of the invention and methods of treating neurodegenerative or neuropsychiatric diseases and disorders using the compounds of the invention, in particular Parkinson's disease.

24 Claims, 1 Drawing Sheet

(56) References Cited

U.S. PATENT DOCUMENTS

2024/0352055 A1    10/2024    Juhl et al.

FOREIGN PATENT DOCUMENTS

| | | |
|---|---|---|
| GB | 2 192 394 A | 1/1998 |
| JP | S60-172975 A | 9/1985 |
| JP | 2007-532670 A | 11/2007 |
| JP | 2010-536889 A | 12/2010 |
| WO | WO 90/12574 A1 | 11/1990 |
| WO | WO 97/03054 A1 | 1/1997 |
| WO | WO 98/38155 A1 | 9/1998 |
| WO | WO 00/47571 A1 | 8/2000 |
| WO | WO 01/36428 A1 | 5/2001 |
| WO | WO 01/76602 A1 | 10/2001 |
| WO | WO 01/78713 A1 | 10/2001 |
| WO | WO 02/13827 A1 | 2/2002 |
| WO | WO 02/14279 A1 | 2/2002 |
| WO | WO 02/100377 A1 | 12/2002 |
| WO | WO 03/006458 A1 | 1/2003 |
| WO | WO 03/013532 A1 | 2/2003 |
| WO | WO 03/074511 A1 | 9/2003 |
| WO | WO 03/080074 A1 | 10/2003 |
| WO | WO 2004/052841 A1 | 6/2004 |
| WO | WO 2005/062894 A2 | 7/2005 |
| WO | WO 2006/012640 A2 | 2/2006 |
| WO | WO 2006/056604 A1 | 6/2006 |
| WO | WO 2009/026934 A1 | 3/2009 |
| WO | WO 2009/026935 A1 | 3/2009 |
| WO | WO 2009/156458 A1 | 12/2009 |
| WO | WO 2010/097091 A1 | 9/2010 |
| WO | WO 2010/097092 A1 | 9/2010 |
| WO | WO 2013/020979 A1 | 2/2013 |
| WO | WO 2013/034119 A1 | 3/2013 |
| WO | WO 2015/067927 A1 | 5/2015 |
| WO | WO 2016/065019 A1 | 4/2016 |
| WO | WO 2017/184871 A1 | 10/2017 |
| WO | WO 2019/101917 A1 | 5/2019 |
| WO | WO 2020/234271 A1 | 11/2020 |

OTHER PUBLICATIONS

International Search Report and Written Opinion for Application No. PCT/EP2020/063915 mailed Jul. 13, 2020.
International Search Report and Written Opinion for Application No. PCT/EP2020/063916 mailed Sep. 28, 2020.
Ahari et al., A direct stereoselective approach to trans-2,3-disubstituted piperidines: application in the synthesis of 2-Epi-CP-99,994 and (+)-epilupinine. Org Lett. Jun. 19, 2008;10(12):2473-6. doi: 10.1021/ol800722a. Epub May 14, 2008.
Alexander et al., Functional architecture of basal ganglia circuits: neural substrates of parallel processing. Trends Neurosci. Jul. 1990;13(7):266-71.
Atkinson et al., Derivatives of apomorphine and of other N-substituted norapomorphines. J Pharm Sci. Nov. 1976;65(11):1682-5.
Bibbiani et al., Continuous dopaminergic stimulation reduces risk of motor complications in parkinsonian primates. Exp Neurol. Mar. 2005;192(1):73-8.
Billeter et al., 8-Hydroxyflavonoid Glucuronides from Malva Sylvestris. Phytochemistry. 1991; 30(3):987-90.
Brown et al., Structurally constrained hybrid derivatives containing octahydrobenzo[g or f]quinoline moieties for dopamine D2 and D3 receptors: binding characterization at D2/D3 receptors and elucidation of a pharmacophore model. J Med Chem. Dec. 25, 2008;51(24):7806-19. doi: 10.1021/jm8008629.
Campbell et al., Behavioral effects of (-)10,11-methylenedioxy-N-n-propylnoraporphine, an orally effective long-acting agent active at central dopamine receptors, and analogous aporphines. Neuropharmacology. Oct. 1982;21(10):953-61.
Cannon et al., N-Alkyl derivatives of trans-6,7-dihydroxy-1,2,3,4,4a,5,10,10b-octahyrobenzo[g]quinoline A congener of apomorphine lacking the non-oxygenated aromatic ring. J. Heterocyclic Chem. Nov. 1980; 17:1633-1636.

Cavero et al., Safety Pharmacology assessment of drugs with biased 5-HT(2B) receptor agonism mediating cardiac valvulopathy. J Pharmacol Toxicol Methods. Mar.-Apr. 2014. 69(2):150-61. doi: 10.1016/j.vascn.2013.12.004. Epub Dec. 19, 2013.
Delong, Primate models of movement disorders of basal ganglia origin. Trends Neurosci. Jul. 1990; 13(7):281-5.
Fan et al., Differential effects of pro-BDNF on sensory neurons after sciatic nerve transection in neonatal rats. Eur J Neurosci. May 2008;27(9):2380-90. doi: 10.1111/j.1460-9568.2008.06215.x. Epub Apr. 22, 2008.
Fan et al., Modifications of the isonipecotic acid fragment of SNS-032: analogs with improved permeability and lower efflux ratio. Bioorg Med Chem Lett. Dec. 1, 2008;18(23):6236-9. doi: 10.1016/j.bmcl.2008.09.099. Epub Oct. 2, 2008. (citation on PubMed).
Fumeaux et al., First synthesis, characterization, and evidence for the presence of hydroxycinnamic acid sulfate and glucuronide conjugates in human biological fluids as a result of coffee consumption. Org Biomol Chem. Nov. 21, 2010;8(22):5199-211. doi: 10.1039/c0ob00137f. Epub Sep. 14, 2010.
Gerfen et al., D1 and D2 dopamine receptor-regulated gene expression of striatonigral and striatopallidal neurons. Science. Dec. 7, 1990;250(4986):1429-32.
Giardina et al., Adrogolide HCl (ABT-431; DAS-431), a prodrug of the dopamine D1 receptor agonist, A-86929: preclinical pharmacology and clinical data. CNS Drug Rev. 2001 Fall;7(3):305-16.
Goswami et al., Intestinal absorption and metabolism of retinoyl beta-glucuronide in humans, and of 15-[14C]-retinoyl beta-glucuronide in rats of different vitamin A status. J Nutr Biochem. Dec. 2003;14(12):703-9.
Grosset et al., Inhaled dry powder apomorphine (VR040) for 'off' periods in Parkinson's disease: an in-clinic double-blind dose ranging study. Acta Neurol Scand. Sep. 2013;128(3):166-71. doi: 10.1111/ane.12107. Epub Mar. 26, 2013.
Hauser et al., Sublingual apomorphine (APL-130277) for the acute conversion of Off to On in Parkinson's disease. Mov Disord. Sep. 2016;31(9):1366-72. Epub Jul. 19, 2016.
Knobloch et al., Keto Esters Derived from 2-(Trimethylsilyl) ethanol: An Orthogonal Protective Group for β-Keto Esters. Synthesis 2008.14 (2008): 2229-2246.
Kotsuki et al., Highly practical, enantiospecific synthesis of the cyclohexyl fragment of the immunosuppressant FK-506. J Org Chem. Aug. 1992;57(18):5036-40.
Liu et al., A novel synthesis and pharmacological evaluation of a potential dopamine D1/D2 agonist: 1-propyl-1,2,3,4,4a,5,10,10a-octahydrobenzo[g]quinoline-6,7-diol. Bioorg Med Chem. Mar. 15, 2008;16(6):3438-44. doi: 10.1016/j.bmc.2007.06.036. Epub Jun. 23, 2007.
Liu et al., Extremely potent orally active benzo[g]quinoline analogue of the dopaminergic prodrug: 1-propyl-trans-2,3,4,4a,5,7,8,9,10,10a-decahydro-1H-benzo-[g]quinolin-6-one [corrected]. J Med Chem. Feb. 23, 2006;49(4):1494-8. Erratum in: J Med Chem. Nov. 16, 2006;49(23):6930.
Loozen et al., An approach to the synthesis of [2] benzopyrano [3, 4?c] pyrroles; alternative dopaminergic molecules. Recueil des Travaux Chimiques des Pays?Bas. 1982;101(9):298-310.
Morissette et al., High-throughput crystallization: polymorphs, salts, co-crystals and solvates of pharmaceutical solids. Adv Drug Deliv Rev. Feb. 23, 2004;56(3):275-300. doi: 10.1016/j.addr.2003.10.020.
Nolen et al., Budesonide-beta-D-glucuronide: a potential prodrug for treatment of ulcerative colitis. J Pharm Sci. Jun. 1995;84(6):677-81.
Poewe et al., Parkinson disease. Nat Rev Dis Primers. Mar. 23, 2017;3:17013.
Rothman et al., Evidence for possible involvement of 5-HT(2B) receptors in the cardiac valvulopathy associated with fenfluramine and other serotonergic medications. Circulation. Dec. 5, 2000;102(23):2836-41.
Sozio et al., Designing prodrugs for the treatment of Parkinson's disease. Expert Opin Drug Discov. May 2012;7(5):385-406. Epub Apr. 12, 2012.
Sprenger et al., Management of motor and non-motor symptoms in Parkinson's disease. CNS Drugs. Apr. 2013;27(4):259-72.

(56) References Cited

OTHER PUBLICATIONS

Stain-Texier et al., Intestinal absorption and stability of morphine 6-glucuronide in different physiological compartments of the rat. Drug Metab Dispos. May 1998;26(5):383-7.
Zhang et al., Flavonoid metabolism: the synthesis of phenolic glucuronides and sulfates as candidate metabolites for bioactivity studies of dietary flavonoids. Tetrahedron. 2012; 68:4194-4201.
Banker et al., Modern Pharmaceuticals. Third Edition, Revised and Expanded. Marcel Dekker, Inc., New York, 1996. p. 596.
David et al., Control of catalytic debenzylation and dehalogenation reactions during liquid-phase reduction by $H_2$. Journal of Catalysis. 2006; 237(2): 349-358.
Kummerer, K. Pharmaceuticals in the Environment. Annu. Rev. Environ. Resour. 2010. 35:57-75. doi: 10.1146/annurev-environ-052809-161223.
Levin et al., Cognitive and neuropsychiatric disorders in extrapyramidal diseases. Neurology, Neuropsychiatry, Psychosomatics. 2012;4(2S):22-30. https://doi.org/10.14412/2074-2711-2012-2505.
Mironov, The Guidelines for Preclinical Trials of Medicinal Products. Grif & Co. Moscow, Russia. 2012. 941 pages.
Przedborski et al., Neurodegeneration: What is it and where are we? J Clin Invest. 2003;111(1):3-10. https://doi.org/10.1172/JCI17522.
Sun et al., Oral bioavailability and brain penetration of (-)-stepholidine, a tetrahydroprotoberberine agonist at dopamine D(1) and antagonist at D(2) receptors, in rats. Br J Pharmacol. Nov. 2009; 158(5):1302-12. Epub Sep. 25, 2009.
Szajewska, H. Evidence-based medicine and clinical research: both are needed, neither is perfect. Ann Nutr Metab. 2018;72 Suppl 3:13-23. doi: 10.1159/000487375. Epub Apr. 9, 2018. PMID: 29631266.
Ugrumov M.V., Development of preclinical diagnosis and preventive treatment of neurodegenerative diseases. Zh Nevrol Psikhiatr Im S S Korsakova. 2015;115(11):4-14. Russian. doi: 10.17116/jnevro20151151114-14.
Wesserling et al., Will in vitro tests replace animal models in experimental oncology? J Tissue Scie Eng. 2011; 2:102e. doi: 10.4172/2157-7552.1000102e.
Wolff, M.E. Burger's Medicinal Chemistry and Drug Discovery. vol. 1, Principles and Practice, Fifth Edition. John Wiley & Sons 1995. pp. 975-977.
International Search Report and Written Opinion for Application No. PCT/EP2020/063918 mailed Aug. 10, 2020.
Di Stefano et al., Antiparkinson prodrugs. Molecules. Jan. 16, 2008;13(1):46-68.
Byrn et al., Pharmaceutical Solids: A Strategic Approach to Regulatory Considerations. Pharmaceutical Research. 1995;12(7):945-54.
Caira, Crystalline Polymorphism of Organic Compounds. Design of Organic Solids. Topics in Current Chemistry.1998(198):163-208.
Choi et al., Dopamine Agonists. NIH National Library of Medicine, In: StatPearls [Internet].Treasure Island (FL): StatPearls Publishing; Jan. 2024. Last updated Jun. 26, 2023. 8 pages.
Clarke, Recent developments in the homogeneous hydrogenation of carboxylic acid esters. Catal. Sci. Technol. Sep. 25, 2012;2:2418-23.
Elger et al., Estrogen sulfamates: a new approach to oral estrogen therapy. Reprod Fertil Dev. 2001;13(4):297-305. doi: 10.1071/rd01029.
Elger et al., Novel oestrogen sulfamates: a new approach to oral hormone therapy. Expert Opin Investig Drugs. Apr. 1998;7(4):575-89. doi: 10.1517/13543784.7.4.575.
Elger et al., Sulfamates of various estrogens are prodrugs with increased systemic and reduced hepatic estrogenicity at oral application. J Steroid Biochem Mol Biol. Dec. 1995;55(3-4):395- 403. doi: 10.1016/0960-0760(95)00214-6.
Fernandez et al., Synthesis and biological studies of glycosyl dopamine derivatives as potential antiparkinsonian agents. Carbohydr Res. Aug. 7, 2000;327(4):353-65. doi: 10.1016/s0008-6215(00)00073-2.
Kuznetsova, Qualitative X-ray phase analysis—Methodological guidelines. Irkutsk State University, General Physics Department. 2005;6 pages.
Malmquist et al., The synthesis of tritiated (R)-2-methoxy-N-n-propyl-nor-apomorphine (MNPA). J Label Compd Radiopharm. Sep. 2007;50(13):1211-1214.
Reutov et al., Organic Chemistry: Manual for Chemical Students and Post-Graduates. 1999; 903-904; 905; 1738-1739 (with reference to N. Kornblum, 1963).
Reutov et al., Organic Chemistry: textbook for students of chemical specialties and graduate students.1999. Chapter 27, Section 27.9.1. c., 1999;6 pages.
Yu, Amorphous pharmaceutical solids: preparation, characterization and stabilization. Adv Drug Deliv Rev. May 16, 2001;48(1):27-42. doi: 10.1016/s0169-409x(01)00098-9.
Yujian et al., Prodrug: Design and Clinical Application. Int J Pharm Res. Oct. 2008;5(35): 377-380, 387.
Khalafi-Nezhad et al., Efficient and Selective Protection of Alcohols and Phenols with Triisopropylsilyl Chloride/Imidazole Using Microwave Irradiation. Tetrahedron. Apr. 4, 2000; 56(38): 7503-7506. doi.org/10.1016/S0040-4020(00)00638-4.
Murakami et al., Practical, modular, and general synthesis of benzofurans through extended Pummerer annulation/cross-coupling strategy. Angew Chem Int Ed Engl. Jul. 14, 2014;53(29):7510-3. doi: 10.1002/anie.201403288. Epub Jun. 12, 2014.

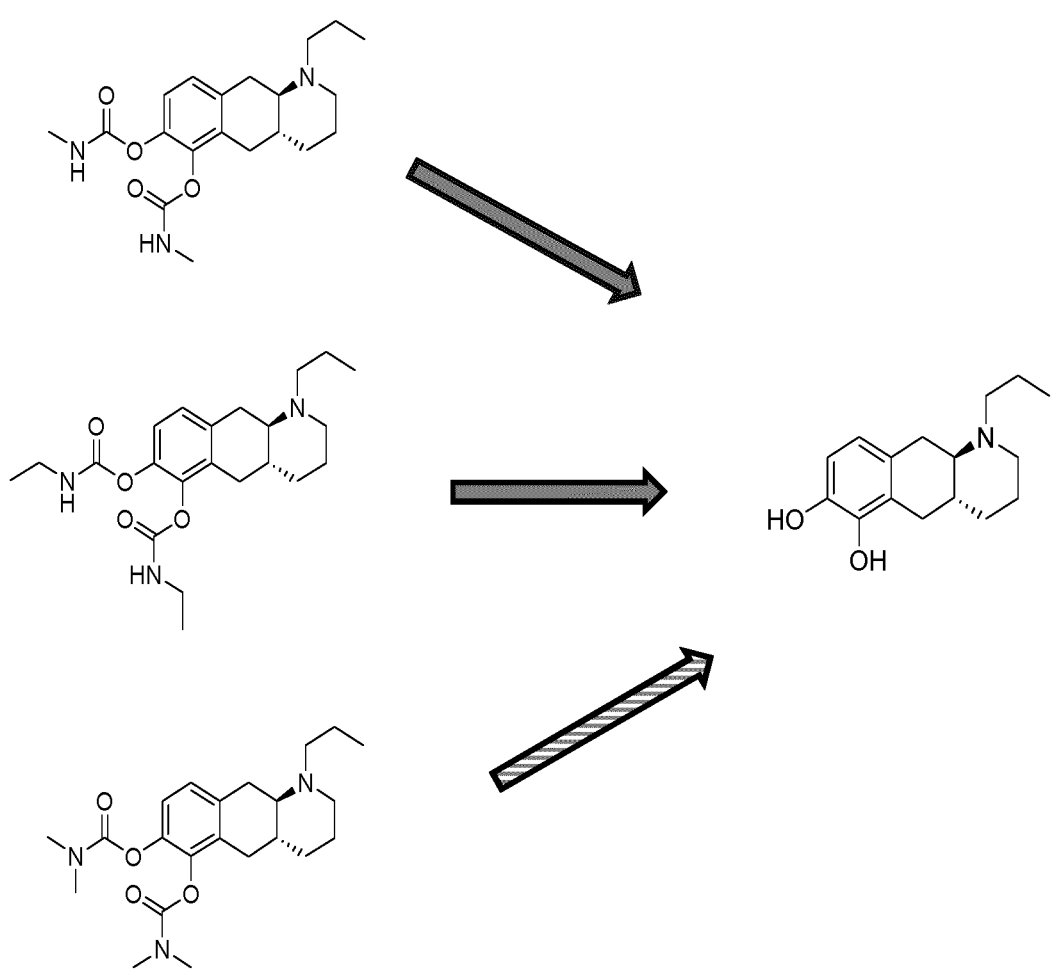

CATECHOLAMINE CARBAMATE PRODRUGS FOR USE IN THE TREATMENT OF PARKINSON'S DISEASE

CROSS REFERENCE TO RELATED APPLICATIONS

This Application is a National Stage filing under 35 U.S.C. 371 of International PCT Application No. PCT/EP2020/063918, filed May 19, 2020, which claims priority to Denmark Application Number PA201900606, filed May 21, 2019, and Denmark Application Number PA201900631, filed May 24, 2019. The entire contents of these applications are incorporated herein by reference in their entirety.

FIELD OF THE INVENTION

The present invention provides compounds that are carbamate derivatives and prodrugs of the dopamine agonist (4aR,10aR)-1-Propyl-1,2,3,4,4a,5,10,10a-octahydro-benzo[g]quinoline-6,7-diol, as well as their use in the treatment of Parkinson's disease and/or other conditions for which treatment with a dopamine agonist is therapeutically beneficial such as but not limited to Restless leg syndrome, Huntington's disease and Alzheimer's disease; and also neuropsychiatric diseases and disorders such as but not limited to schizophrenia, attention deficit hyperactivity disorder and drug addiction. The present invention also provides pharmaceutical compositions comprising compounds of the invention.

BACKGROUND OF THE INVENTION

Parkinson's disease (PD) is a common neurodegenerative disorder that becomes increasingly prevalent with age and affects an estimated seven to ten million people worldwide. Parkinson's disease is a multi-faceted disease characterized by both motor and non-motor symptoms. Motor symptoms include resting tremor (shaking), bradykinesia/akinesia (slowness and poverty of movements), muscular rigidity, postural instability and gait dysfunction; whereas non-motor symptoms include neuropsychiatric disorders (e.g. depression, psychotic symptoms, anxiety, apathy, mild-cognitive impairment and dementia) as well as autonomic dysfunctions and sleep disturbances (Poewe et al., Nature Review, (2017) vol 3 article 17013: 1-21).

A key hallmark of Parkinson's disease pathophysiology is the loss of pigmented dopaminergic neurons in the substantia nigra pars *compacta* that provides dopaminergic innervation to the striatum and other brain areas. Such progressive neurodegeneration leads to the decrease in dopamine striatal levels which ultimately results in a series of changes in the basal ganglia circuitry, ultimately ending up in the occurrence of the four cardinal motor features of Parkinson's disease. The main target of dopamine in the striatum consists of medium spiny GABAergic neurons (MSNs) selectively expressing D1 or D2 receptors pending topographical projections. GABAergic-MSN projecting to the external *pallidum*, also called striato-pallidal 'indirect pathway' express D2 receptors (MSN-2); whereas GABAergic-MSN projecting to the substantia nigra pars *reticulata* and internal *pallidum*, also called striato-nigral 'direct pathway' express D1 receptors (MSN-1). Depletion of dopamine because of neuronal loss results in an imbalanced activity of the two pathways, resulting in a marked reduction of thalamic and cortical output activities and ultimately motor dysfunctions (Gerfen et al, Science (1990) 250: 1429-32; Delong, (1990) Trends in Neuroscience 13: 281-5; Alexander et Crutcher, (1990) Trends in Neuroscience 13: 266-71; and for review Poewe et al., Nature Review (2017) vol. 3 article 17013: 1-21).

The most effective therapeutic strategies available to patients suffering from Parkinson's disease, and aiming at controlling motor symptoms are primarily indirect and direct dopamine agonists. The classic and gold standard treatment regimen includes chronic oral intake of L-3,4-dihydroxy phenylalanine (L-DOPA) which is decarboxylated in the brain to form dopamine. Other approaches consist in the administration of dopamine receptor agonists such as apomorphine which acts both on the D1 and D2 receptors subtypes, or pramipexole, ropinirole and others which are predominantly directed towards D2 receptors subtypes. Optimal motor relief is obtained with use of both L-DOPA and apomorphine due to their activation of both D1 and D2 receptor subtypes and holistic re-equilibrium of the indirect-direct pathways (i.e. while D2 agonists only reverse the indirect pathway dysfunction).

L-DOPA and apomorphine with the structures depicted below are currently the most efficacious PD drugs in clinical use.

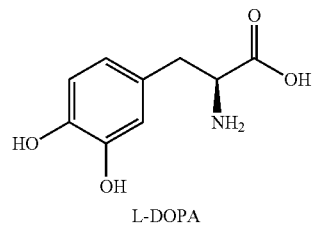

L-DOPA

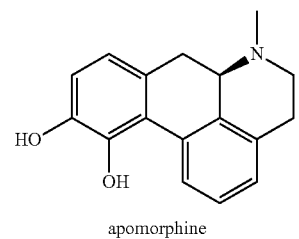

apomorphine

L-DOPA is a prodrug of dopamine and remains the most efficacious drug in the treatment of motor Parkinson's disease. However, after several years of treatment (i.e. honeymoon period), complications arise due the inherent progression of the disease (i.e. sustained loss of dopaminergic neurons) as well as poor pharmacokinetic (PK) profile of L-DOPA. Those complications include: 1) dyskinesia which are abnormal involuntary movements occurring during the optimal 'on-time effect' of the drug; and 2) off fluctuations, period during which the L-DOPA positive effect wears off and symptoms re-emerge or worsen (Sprenger and Poewe, CNS Drugs (2013), 27: 259-272).

Direct dopamine receptor agonists are able to activate the dopamine auto receptors as well as the postsynaptic dopamine receptors located on the medium spiny neurons MSN-1 and MSN-2. Apomorphine belongs to a class of dopamine agonists with a 1,2-dihydroxybenzene (catechol) moiety. When combined with a phenethylamine motif, catecholamines often possess low or no oral bioavailability as is the case for apomorphine. Apomorphine is used clinically in PD therapy albeit with a non-oral delivery (typically intermittent subcutaneous administration or daytime continuous parenteral infusion via a pump). For apomorphine, animal studies have shown that transdermal delivery or implants may provide possible forms of administration. However, when the delivery of apomorphine from implants was studied in monkeys (Bibbiani et al., Chase Experimental Neurology (2005), 192: 73-78) it was found that in most cases the animals had to be treated with the immunosuppressant dexamethasone to prevent local irritation and other complications following the implantation surgery. Alternative delivery strategies for apomorphine therapy in PD such as inhalation and sublingual formulations have been extensively explored (see e.g. Grosset et al., Acta Neurol Scand. (2013), 128:166-171 and Hauser et al., Movement Disorders (2016), Vol. 32 (9): 1367-1372). However, these efforts are yet not in clinical use for the treatment of PD.

An alternative to the non-oral formulations of the catecholamines involves the use of a prodrug masking the free catechol hydroxyl groups to enable oral administration. However, a known problem associated with the development of prodrugs for clinical use is the difficulties associated with predicting conversion to the parent compound in humans.

Various ester prodrugs of catecholamines have been reported in the literature such as enterically coated N-propyl-noraporphine (NPA) and the mono pivaloyl ester of apomorphine for duodenal delivery (see eg. WO 02/100377), and the D1-like agonist adrogolide, a diacetyl prodrug of A-86929 (Giardina and Williams; CNS Drug Reviews (2001), Vol. 7 (3): 305-316). Adrogolide undergoes extensive hepatic first-pass metabolism in man after oral dosing and, as a result, has a low oral bioavailability (app. 4%). In PD patients, intravenous (IV) adrogolide has antiparkinson efficacy comparable to that of L-DOPA (Giardina and Williams; CNS Drug Reviews (2001), Vol. 7 (3): 305-316).

In addition to the ester prodrugs of catecholamines, an alternative prodrug approach involves the masking of the two catechol hydroxyl groups as the corresponding methylene-dioxy derivative or di-acetalyl derivative. This prodrug principle has been described for example in Campbell et al., Neuropharmacology (1982); 21(10): 953-961 and in U.S. Pat. No. 4,543,256, WO 2009/026934 and WO 2009/026935.

Yet another suggested approach for a catecholamine prodrug is the formation of an enone derivative as suggested in for example WO 2001/078713 and in Liu et al., Bioorganic Med. Chem. (2008), 16: 3438-3444. For further examples of catecholamine prodrugs see for example Sozio et al., Exp. Opin. Drug Disc. (2012); 7(5): 385-406.

The compound (4aR,10aR)-1-Propyl-1,2,3,4,4a,5,10,10a-octahydro-benzo[g]quinoline-6,7-diol depicted as compound (I) below is disclosed in WO 2009/026934. The trans-isomer was disclosed previously in Liu et al., J. Med. Chem. (2006), 49: 1494-1498 and then in Liu et al., Bioorganic Med. Chem. (2008), 16: 3438-3444 including pharmacological data indicating that the compound has a low oral bioavailability in rats. The racemate was disclosed for the first time in Cannon et al., J. Heterocyclic Chem. (1980); 17: 1633-1636.

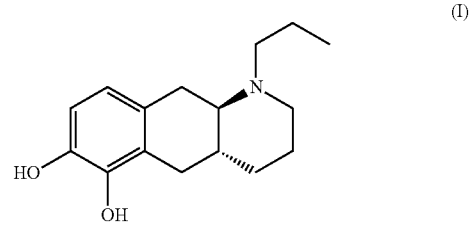 [SMILES: CCCN1CCC[C@@H]2Cc3c(ccc(O)c3O)C[C@H]21]

(I)

Compound (I) is a dopamine receptor agonist with mixed D1 and D2 activity. Three prodrug derivatives of compound (I) are known in the art.

Liu et al., J. Med. Chem. (2006), 49: 1494-1498 and Liu et al., Bioorganic Med. Chem. (2008), 16: 3438-3444 disclose the enone derivative of formula (Ia) depicted below which was shown to be converted to the active compound (I) in rats.

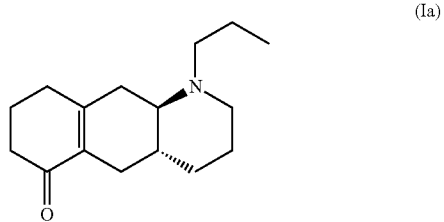 [SMILES: CCCN1CCC[C@@H]2CC3=C(CCCC3=O)C[C@H]21]

(Ia)

WO 2009/026934 and WO 2009/026935 disclose two types of prodrug derivatives of compound (I) including (6aR,10aR)-7-propyl-6,6a,7,8,9,10,10a,11-octahydro-[1,3]dioxolo[4',5':5,6]benzo[1,2-g]quinoline, a methylenedioxy (MDO) derivative with the formula (Ib) below:

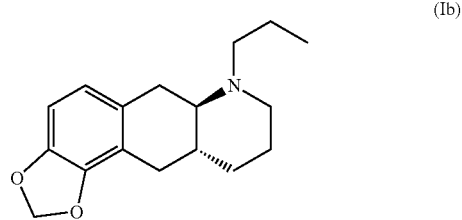 [SMILES: CCCN1CCC[C@@H]2Cc3c(ccc4c3OCO4)C[C@H]21]

(Ib)

The conversion of compound (Ib) to compound (I) in rat and human hepatocytes has been demonstrated in WO 2010/097092. Furthermore, the in vivo pharmacology of the compounds (Ia) and (Ib) as well as the active "parent compound" (1) has been tested in various animal models relevant for Parkinson's Disease (WO 2010/097092). Both compound (I) and compounds (Ia) and (Ib) were found to be effective, indicating that compounds (Ia) and (Ib) are converted in vivo to compound (I). All three compounds were reported to have a duration of action that was longer than observed for L-dopa and apomorphine.

The other prodrug of compound (I) disclosed in WO 2009/026934 and WO 2009/026935 is a conventional ester prodrug of the formula (Ic)

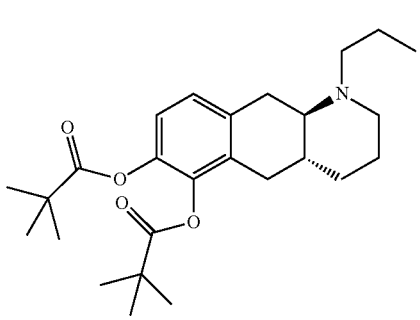

(Ic)

Despite the long-standing interest in the field, there is evidently still an unmet need as regards developing efficient, well-tolerated and orally active drugs for the treatment of PD. A prodrug derivative of a mixed D1/D2 agonist giving a stable PK profile which can provide continuous dopaminergic stimulation may fulfil such unmet needs.

Carbamate derivatives as prodrug principle have previously been suggested and explored for various compounds including catechol moieties. Carbamate derivatives of apomorphine and N-n-propylnorapomorphine has been suggested as prodrug derivatives decades ago (Edward et al. (1976). J. Pharm Sci. 65(11): 1682-1685). Apomorphine Bis(dimethylcarbamate) has been synthesized and tested in mice albeit with very limited pharmacological effect compared to apomorphine itself suggesting a very slow conversion to apomorphine. EP0352815 demonstrates oral bioavailability of carbamate derivatives of gamma-L-glutamyl-L-dopa for treatment of Parkinson's Disease.

Prodrugs targeting various amino acid or peptide transporters are known in the art (see e.g. Vale et al. 2018, Amino acids in the development of prodrugs, Molecules, 23(9), 2318.) Further, Ninomiya et al. (2011), discloses amino acid conjugates of tricin and mentions improved bioavailability after oral administration. Further, Kim et al. reported that quercetin-amino acid derivatives demonstrate favourable cell permeability in vitro through interaction with the peptide transporter PEPT1 ((In vitro solubility, stability and permeability of novel quercetin-amino acid (Kim, M. K.; Park, K.-S.; Yeo, W.-S.; Choo, H.; Chong, Y. In vitro solubility, stability and permeability of novel quercetin-amino acid conjugates. Bioorg. Med. Chem. 2009, 17, 1164-1171.) WO06014429 discloses prodrugs to cidofovir, which comprise amino acid residues or peptides and which have affinity for hPEPT1. None of these documents however, disclose a catechol amine prodrug comprising amino acids or peptide moieties.

SUMMARY OF THE INVENTION

The present invention relates to new compounds for treatment of Parkinson's Disease. More particularly, the invention relates to new carbamate prodrug derivatives of the compound (4aR,10aR)-1-Propyl-1,2,3,4,4a,5,10,10a-octahydro-benzo[g]quinoline-6,7-diol (compound (I)). Representative compounds (1)-(3) of the invention have proven particularly useful for oral delivery of compound (I).

Thus, in a first aspect, is provided a compound according to formula (Ie)

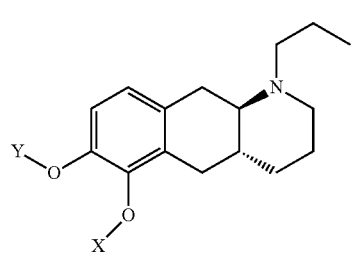

(Ie)

wherein Y is selected from H and a carbamoyl group of the formula CONR1R2 below

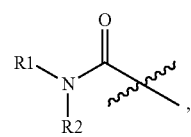

(CONR1R2)

and
wherein X is selected from H and a carbamoyl group of the formula CONR3NR4 below

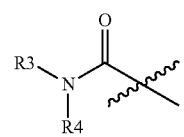

(CONR3R4)

wherein Y and X are not both H, and
wherein R1, R2, R3 and R4 are each individually selected from the group consisting of H, $C_{1-6}$ alkyl, an amino acid, an amino acid residue and a peptide;
or a pharmaceutically acceptable salt thereof.

In another aspect, the invention relates to a pharmaceutical composition comprising a compound according formula (Id) or a pharmaceutically acceptable salt thereof, and one or more pharmaceutically acceptable excipients.

A further aspect of the invention relates to a compound according to formula (Id) for use as a medicament.

A further aspect of the invention relates to a compound according to formula (Id) or a pharmaceutically acceptable salt thereof for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

A further aspect of the invention relates to a method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of a compound of formula (Id) or a pharmaceutically acceptable salt thereof, to a patient in need thereof.

A further aspect of the invention relates to the use of a compound according to formula (Id) or a pharmaceutically acceptable salt thereof, for the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

Definitions

Compounds of the Invention

Reference to compounds encompassed by the invention includes the free substance (e.g. a free base or a zwitter ion) of compounds of the invention, pharmaceutically acceptable salts of compounds of the invention, such as acid addition salts or base addition salts, and polymorphic and amorphic forms of compounds of the invention and of pharmaceutically acceptable salts thereof. Furthermore, the compounds of the invention and pharmaceutically acceptable salts thereof may potentially exist in unsolvated as well as in solvated forms with pharmaceutically acceptable solvents such as water, ethanol and the like. Both solvated and unsolvated forms are encompassed by the present invention.

Pharmaceutically Acceptable Salts

Pharmaceutically acceptable salts in the present context is intended to indicate non-toxic, i.e. physiologically acceptable salts.

The term "pharmaceutically acceptable salts" include pharmaceutically acceptable acid addition salts which are salts formed with inorganic and/or organic acids on the nitrogen atom in the parent molecule. Said acids may be selected from for example hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, malonic acid, fumaric acid, glutamic acid, pyroglutamic acid, salicylic acid, gentisic acid, saccharin, and sulfonic acids such as methanesulfonic acid, ethanesulfonic acid, toluenesulfonic acid, naphthalene-2-sulphonic acid, 2-hydroxy ethanesulphonic acid and benzenesulfonic acid.

Additional examples of useful acids to form pharmaceutically acceptable salts can be found e.g. in Stahl and Wermuth (Eds) "Handbook of Pharmaceutical salts. Properties, selection, and use", Wiley-VCH, 2008.

Prodrug

In the present context, the terms "prodrug" or "prodrug derivative" indicates a compound that, after administration to a living subject, such as a mammal, preferably a human; is converted within the body into a pharmacologically active moiety. The conversion preferably takes place within a mammal, such as in a mouse, rat, dog, minipig, rabbit, monkey and/or human. In the present context a "prodrug of the compound (4aR,10aR)-1-Propyl-1,2,3,4,4a,5,10,10a-octahydro-benzo[g]quinoline-6,7-diol" or "a prodrug of the compound of formula (I)" or "a prodrug of compound (I)" is understood to be a compound that, after administration, is converted within the body into the compound (4aR,10aR)-1-Propyl-1,2,3,4,4a,5,10,10a-octahydro-benzo[g]quinoline-6,7-diol. Said administration may be by any conventional route of administration of pharmaceutical compositions known in the art, preferably by oral administration.

In the present context, the terms "parent compound" and "parent molecule" indicate the pharmacologically active moiety obtained upon conversion of a corresponding prodrug. For example, the "parent compound" of one of the compounds (Ia), (Ib), (Ic) or any of the compounds of the invention is understood to be the compound of formula (I).

Substituents

In the present context, a given range may interchangeably be indicated with "-" (dash) or "to", e.g. the term "$C_1$-$C_6$ alkyl" is equivalent to "$C_1$ to $C_6$ alkyl".

The term "alkyl" refer to a linear (i.e. unbranched) or branched saturated hydrocarbon having from one up to six carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl and n-hexyl.

Amino Acid

An amino acid can be based on any one of the twenty common amino acids found in naturally synthesized proteins as long as the residue provides for the oral bioavailability of a compound (I) of the present invention. Common amino acids include arginine, lysine, aspartic acid, glutamic acid, glutamine, asparagine, histidine, serine, threonine, tyrosine, cysteine, tryptophan, methionine, alanine, isoleucine, leucine, phenylalanine, valine, proline and glycine.

Alpha-amino acids having both the amino and the carboxylic acid groups attached to the first α-carbon atom are preferred in some embodiments of the invention. The amino group attached to the α-carbon is sometimes called the α-amino group. Similarly, the carboxylic acid group attached to the α-carbon is sometimes called the α-carboxyl group. Except for the cyclic amino acid proline, α-amino acids have the generic formula H2NC$^α$HXCOOH wherein X is an organic substituent known as a "side chain", and the remaining part is known as the back bone, wherein the backbone has a (α-) carboxyl group and an (α-) amino group.

The term "amino acid residue" means an amino acid lacking a portion of its structure. Thus, for example, when the term an amino acid residue that is glycine is mentioned herein, it will be understood that the amino acid residue is a glycine lacking a portion of its structure. Examples include an α-amino acid without the OH portion of the α-carboxyl group, or lacking the H portion of the α-amino group. Also included within the definition of an amino acid residue is an amino acid lacking a portion of its side chain, such as a serine amino acid lacking the H portion of the side chain —OH group.

An amino acid residue can also be based on a modified or unusual amino acid. Examples of modified or unusual amino acids include, but are not limited to, 2-aminoadipic acid, 3-aminoadipic acid, beta-alanine, 2-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allohydroxylysine, 3-hydroxyproline, 4-hydroxyproline, isodesmosine, isodesmosine, N-methylglycine, N-methylisoleucine, N-methylvaline, norvaline, norleucine, ornithine and homoserine.

Similarly, a peptide, such as a dipeptide or tripeptide can comprise any of the twenty common amino acids and any of the modified or unusual amino acids as long as the peptide supports the oral bioavailability of the compound (I)-carbamate derivate.

Both the (D) and (L) stereoisomers of an amino acid residue can be incorporated into the compounds of the invention. When the configuration is not designated, the amino acid or residue can have the configuration (D), (L) or (DL). For the purposes of this application, unless expressly noted to the contrary, a named amino acid shall be construed to include both the (D) or (L) stereoisomers. In a specific embodiment of the invention, an amino acid residue is a L-amino acid, and a peptide is prepared from L-amino acids.

A derivative of an amino acid residue is an amino acid residue having a portion of its structure substituted by an atom or molecular group. Examples of such derivatives include, but are not limited to, ester derivatives having an —OR group substituting for the α-carboxyl —OH group, where R is an alkyl or alkenyl group. In specific embodiments, R is a C1-C20 alkyl or alkenyl group. A dipeptide or tripeptide derivative is a peptide that contains at least one derivative of an amino acid residue.

Pharmacokinetic Definitions and Abbreviations

As used herein, a "PK profile" is an abbreviation of "pharmacokinetic profile". Pharmacokinetic profiles and pharmacokinetic parameters described herein are based on the plasma concentration-time data obtained for the compound of formula (I) after oral dosing of a compound of the invention, using non-compartmental modelling. Abbreviated PK parameters are: $C_{max}$ (maximum concentration); $t_{max}$ (time to $C_{max}$); $t_{1/2}$ (half-life); $AUC_{024}$ (area under the curve from time of dosing and until 24 hours after dosing, and "Exposure at 24 h" is the plasma concentration of the compound of formula (I) as measured 24 hours after dosing.

Therapeutically Effective Amount

In the present context, the term "therapeutically effective amount" of a compound of the invention means an amount sufficient to alleviate, arrest, partly arrest, remove or delay the clinical manifestations of a given disease and its complications in a therapeutic intervention comprising the administration of said compound. An amount adequate to accomplish this is defined as "therapeutically effective amount". Effective amounts for each purpose will depend e.g. on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the context of the present invention, a "therapeutically effective amount" of a compound of the invention indicates an amount of said compound of the invention that is able to provide an amount of compound (I) that is sufficient to alleviate, arrest, partly arrest, remove or delay the clinical manifestations of a given disease and its complications when said compound of the invention is administered, preferably by the oral route, to a mammal, preferably a human.

Treatment and Treating

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

Conditions for Treatment

The compounds of the present invention are intended for treatment of neurodegenerative diseases and disorders such as Parkinson's disease and/or other conditions for which treatment with a dopamine agonist is therapeutically beneficial.

Therapeutic indications include a variety of central nervous system disorders characterized by motor and/or non-motor disturbances and for which part of the underlying pathophysiology is a dysfunction of the striatal-mediated circuitry. Such functional disturbances can be seen in neurodegenerative diseases such as but not limited to Parkinson's disease (PD), Restless leg syndrome, Huntington's disease, and Alzheimer's disease but also neuropsychiatric diseases such as, but not limited to schizophrenia, attention deficit hyperactivity disorder and drug addiction.

In addition to neurodegenerative diseases and disorders, other conditions in which an increase in dopaminergic turnover may be beneficial are in the improvement of mental functions including various aspects of cognition. It may also have a positive effect in depressed patients, and it may also be used in the treatment of obesity as an anorectic agent and in the treatment of drug addiction. It may improve minimal brain dysfunction (MBD), narcolepsy, attention deficit hyperactivity disorder and potentially the negative, the positive as well as the cognitive symptoms of schizophrenia.

Restless leg syndrome (RLS) and periodic limb movement disorder (PLMD) are alternative indications, which are clinically treated with dopamine agonists. In addition, impotence, erectile dysfunction, SSRI induced sexual dysfunction, ovarian hyperstimulation syndrome (OHSS) and certain pituitary tumors (prolactinoma) are also likely to be improved by treatment with dopamine agonists. Dopamine is involved in regulation of the cardiovascular and renal systems, and accordingly, renal failure and hypertension can be considered alternative indications for the compounds of the invention.

The invention encompasses use of the compounds of the invention for treatment of the diseases and disorders listed above.

Combinations

In one embodiment of the invention, the compounds of formula (Ie) are for use as stand-alone treatment as the sole active compound. In another embodiment of the invention, a compound of formula (Ie) may be used in combination with other agents useful in the treatment of a neurodegenerative disease or disorder such as Parkinson's disease. The terms "combined use", "in combination with" and "a combination of" and the like as used herein in the context of the method of the invention comprising the combined administration of therapeutically effective amounts of a compound of formula (Ie), and another compound, which compound is useful in the treatment a neurodegenerative disease or disorder, is intended to mean the administration of a compound of formula (Ie) simultaneously or sequentially, in any order, together with said other compound.

The two compounds may be administered simultaneously or with a time gap between the administrations of the two compounds. The two compounds may be administered either as part of the same pharmaceutical formulation or composition, or in separate pharmaceutical formulations or compositions. The two compounds may be administered on the same day or on different days. They may be administered by the same route, such for example by oral administration, subcutaneous injection, by transdermal administration, by depot, by intramuscular injection or intravenous injection; or by different routes wherein one compound is for example administered orally or placed by depot and the other compound is for example injected. The two compounds may be administered by the same dosage regime or interval, such as once or twice daily, weekly, or monthly; or by different dosage regimes for example wherein one is administered once daily and the other is administered twice daily or weekly or monthly.

In some instances, the patient to be treated may already be in treatment with one or more other compounds useful in the treatment of a neurodegenerative disease or disorder when treatment with a compound of formula (Ie) is initiated. In other instances, the patient may already be in treatment with a compound of formula (Ie) or (Id) when treatment with one or more other compounds useful in the treatment of a neurodegenerative disease or disorder is initiated. In other instances, the treatment with a compound of formula (Ie) and treatment with one or more other compounds useful in the treatment of a neurodegenerative disease or disorder is initiated at the same time.

Compounds for Combination Treatment

In the context of the invention, compounds to be used in combination with a compound of formula (Ie) may be selected from for example L-DOPA, droxidopa, foliglurax, MAO-B inhibitors such as selegiline or rasagiline, COMT inhibitors such as entacapone or tolcapone, adenosine 2a antagonists such as istradefylline, antiglutamatergic agents such as amantadine or memantine, acetylcholinesterase inhibitors such as rivastigmine, donepezil or galantamine and antipsychotic agents such as quetiapine, clozapine, risperidone, pimavanserin, olanzapine, haloperidol, aripiprazole or brexpiprazole.

In addition to small molecules, compounds for combination could also include emerging biologics approaches in treatments for neurodegenerative diseases or disorders such as for example antibodies targeting alpha-synuclein, Tau or A-beta proteins.

Administration Routes

The pharmaceutical compositions comprising a compound of formula (Ie), either as the sole active compound or in combination with another active compound, may be specifically formulated for administration by any suitable route such as the oral, rectal, nasal, buccal, sublingual, pulmonal, transdermal and parenteral (e.g. subcutaneous, intramuscular, and intravenous) route. In the context of the present invention the oral route is the preferred route of administration.

It will be appreciated that the route will depend on the general condition and age of the subject to be treated, the nature of the condition to be treated and the active ingredient.

Pharmaceutical Formulations and Excipients

In the following, the term, "excipient" or "pharmaceutically acceptable excipient" refers to pharmaceutical excipients including, but not limited to, carriers, fillers, diluents, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound of formula (Ie), such as one of the compounds disclosed in the Experimental Section herein. The present invention also provides a process for making a pharmaceutical composition comprising a compound of formula (Ie). The pharmaceutical compositions according to the invention may be formulated with pharmaceutically acceptable excipients in accordance with conventional techniques such as those disclosed in Remington, "The Science and Practice of Pharmacy", $22^{th}$ edition (2012), Edited by Allen, Loyd V., Jr.

The pharmaceutical composition comprising a compound of the present invention is preferably a pharmaceutical composition for oral administration. Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses

In one embodiment, the compound of the present invention is administered in an amount from about 0.0001 mg/kg body weight to about 5 mg/kg body weight per day. In particular, daily dosages may be in the range of 0.001 mg/kg body weight to about 2 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.01-100 mg/day of a compound of the present invention, such as 0.05-50 mg/day, such as 0.1-10 mg/day or 0.1-5 mg/day. Conveniently, the compounds of the invention are administered in a unit dosage form containing said compounds in an amount of about 0.01 to 50 mg, such as 0.05 mg, 0.1 mg, 0.2 mg, 0.5 mg, 1 mg, 5 mg, 10 mg, 15 mg, 20 mg or up to 50 mg of a compound of the present invention.

BRIEF DESCRIPTION OF FIGURES

FIG. 1: graphic illustration of conversion of compounds (1)-(3) of the invention to compound (I). Solid arrows: conversion demonstrated in vitro and in vivo. Streaky arrow: conversion demonstrated in vivo.

DETAILED DESCRIPTION OF THE INVENTION

The inventors have identified new compounds that are carbamate-derivatives and prodrugs of (4aR,10aR)-1-Propyl-1,2,3,4,4a,5,10,10a-octahydro-benzo[g]quinoline-6,7-diol [compound (I)] which is a dual D1/D2 agonist (see for example WO 2009/026934).

The compounds of the invention are carbamate derivatives of compound (I).

The inventors of the present invention found that oral dosing of representative compounds (1)-(3) of the invention in Wistar rats provides a systemic exposure of compound (I) in plasma, suggesting the usefulness of said compounds as orally active prodrugs of compound (I).

For the compounds tested in vivo, the doses were corrected by molecular weight to equal a dose of 300 µg/kg of compound (Ib) corresponding to 287 µg/kg of compound (I). It was found that oral dosing of compounds (Ia) and (Ib) to Wistar rats results in early and high peak concentrations of compound (I). Such high peak concentrations are in humans likely to be associated with dopaminergic side effects such as for example nausea, vomiting and light headedness. In contrast, for the compounds of the invention a slower absorption rate was observed accompanied by a sustained exposure of compound (I) avoiding rapid peak plasma concentrations. Additionally, the plasma exposure of compound (I) in Wistar rats is maintained throughout 24 hours although the obtained AUC of compound (I) was lower than the AUC obtained after dosing of compounds (Ia) and (Ib). However, since the peak concentrations of compound (I) which are expected to drive the side effects are lower, higher doses may be administered of the compounds of the invention to potentially achieve higher overall plasma concentrations of compound (I) compared to what is achievable from dosing compounds (Ia) and (Ib). When investigating PK properties of compound (Ic), the inventors found that the plasma concentrations of compound (I) were extremely low, leaving compound (Ic) unsuitable as a prodrug of compound (I) for oral administration and confirming that the oral bioavailability of the compounds of the invention is highly unpredictable. PK parameters for the PK studies in Wistar rats are listed in Table 4.

Bioconversion of the compounds (1)-(3) of the invention to the compound of formula (I) has also been assessed by incubation in human plasma as described in Example 1. For the parent compound (I) itself a short half-life in the plasma assay was observed, which likely explains that for one of the compounds of the invention no formation of compound (I) could be determined for as it may have been metabolised at the same time as it was formed. For all compounds (1)-(3) of the invention, conversion to compound (I) was demonstrated either in vivo or both in vivo and in vitro c.f. Table 1 below and in FIG. 1.

TABLE 1 in vitro and in vivo conversion of compounds (1) to (3) of the invention

| | Incubation in human plasma | In vivo PK study after oral dosing (rats) |
|---|---|---|
| | Observed metabolite | |
| Compound (3) | Compound (I) | Compound (I) |
| Compound (2) | Compound (I) | Compound (I) |
| Compound (1) | | Compound (I) |

In conclusion, the compounds of the invention, as represented by compounds (1)-(3) are useful as orally active prodrugs of compound (I) and has been observed in rats to provide a PK profile avoiding the peak $C_{max}$ observed for the known prodrugs (Ia) and (Ib) and providing a significantly higher AUC of compound (I) than compound (Ic).

Finally, an important issue associated with the compound (Ib) is that this compound is an agonist of the 5-HT2B receptor. Since 5-HT2B receptor agonists have been linked to pathogenesis of valvular heart disease (VHD) after long term exposure, such compounds are not suitable for use in the treatment of chronical diseases (Rothman et al., Circulation (2000), 102: 2836-2841; and Cavero and Guillon, J. Pharmacol. Toxicol. Methods (2014), 69: 150-161). Thus, a further advantage of the compounds (1)-(3) of the invention is that these are not 5-HT2B agonists c.f. example 2 and Table 3.

Peptide transporters (PEPT1 and PEPT2) as well as LAT1 and LAT2 haven been used as targets for prodrugs, wherein amino acids or peptides have been linked to an active compound by using ester or carbamate links. L-type amino acid transporters 1 (LAT1) and 2 (LAT2) are responsible for carrying large neutral amino acids from extracellular fluids into the cells. The natural substrates of LAT1 are large neutral amino acids such as L-leucine, L-tryptophan, and L-phenylalanine. Further, the PEPT1 is known to play a critical role in the absorption of diverse drugs and prodrugs from the intestinal tract. PEPT1 is located in the apical enterocytic membrane of the upper small intestine where it serves as a symporter, using an electrochemical proton gradient as its driving force. Human PEPT1 (hPEPT1) contains 708 amino acids oriented in 12 membrane-spanning domains. Since PEPT1 is an important amino acid/di/tri peptide transporter in human enterocytes, the transportation of hundreds of different possible dipeptides, thousands of possible tripeptides, and diverse drugs and prodrugs, implies broad substrate specificity for this transporter.

In one embodiment of the invention, the carbamate-derivative compounds of compound (I) is capable of being transported by one or more peptide transporters, such as PEPT1, PEPT2, LAT1 and LAT2. In a more specific embodiment of the invention, the carbamate-derivative compounds of compound (I) as defined herein are capable of being transported by PEPT1.

PEPT1 has been shown to have high affinity for L-amino acids or peptides comprising L-amino acids. Thus, in one embodiment of the invention, an amino acid or amino acid residue is a L amino acid, or L-amino acid residue. Similarly, in one embodiment of the invention, a peptide is comprising or consisting of L-amino acids.

Amino acids or amino acid residues according to the present invention may be any one of the twenty common amino acids found in naturally synthesized proteins. Thus, in one embodiment, an amino acid or amino acid residue is selected from the group consisting of arginine, lysine, aspartic acid, glutamic acid, glutamine, asparagine, histidine, serine, threonine, tyrosine, cysteine, tryptophan, methionine, alanine, isoleucine, leucine, phenylalanine, valine, proline and glycine.

In one embodiment of the invention, a peptide comprises two or more amino acid residues of amino acids selected from the group consisting of arginine, lysine, aspartic acid, glutamic acid, glutamine, asparagine, histidine, serine, threonine, tyrosine, cysteine, tryptophan, methionine, alanine, isoleucine, leucine, phenylalanine, valine, proline and glycine.

In some studies, PEPT1 has been found to have preference from specific amino acids, or peptides comprising specific amino acids, such as phenylalanine, valine, leucine, isoleucine, glycine and alanine. Thus, in one embodiment of the invention, an amino acid is selected from the group consisting of phenylalanine, valine, leucine, isoleucine, glycine and alanine, wherein the L-form of the amino acids of the group is preferred. In an even more specific embodiment of the invention, an amino acid is selected from the group consisting of phenylalanine, and glycine.

Similarly, in one embodiment, a peptide comprises or consists of one or more amino acids selected from the group consisting of phenylalanine, valine, leucine, isoleucine, glycine and alanine, wherein the L-form of the amino acids of the group is preferred. In an even more specific embodiment of the invention, a peptide comprises one or more amino acids selected from the group consisting of phenylalanine, and glycine.

PEPT1 may transport single amino acid-derivatives of active compounds as well as di peptide-derivatives and tri-peptide derivatives. Thus, in one embodiment of the invention, the carbamate-derivatives of compound (I) comprises one amino acid residue.

In another embodiment of the invention, the compounds of the invention comprise a dipeptide or a tripeptide.

In one embodiment of the invention, the compounds of the invention comprise a dipeptide comprising or consisting of one or more amino acids selected from the group consisting of phenylalanine, valine, leucine, isoleucine, glycine and alanine, wherein the L-form of the amino acids of the group is preferred. In a specific embodiment of the invention, the compounds of the invention comprise a dipeptide comprising or consisting of one or more amino acids or amino acid residues selected from the group consisting of phenylalanine, and glycine. In an even more specific embodiment, the compounds of the invention comprise a dipeptide comprising a phenylalanine residue. In an even more specific embodiment, the compounds of the invention comprise a dipeptide comprising a glycine residue. In a specific embodiment of the invention, the dipeptide consists of a phenylalanine and a glycine residue.

In another specific embodiment, the compounds of the invention comprise a dipeptide comprising or consisting of at least two of the amino acid residues selected from the group consisting of phenylalanine, valine, leucine, isoleucine, glycine and alanine.

In a specific embodiment of the invention, the dipeptide consists of two alanine residues, or of two phenylalanine residues, or of two leucine residues, or of two isoleucine residues, or of two valine residues.

In one embodiment of the invention, the compounds of the invention comprise a tripeptide comprising or consisting of one or more amino acids selected from the group consisting of phenylalanine, valine, leucine, isoleucine, glycine and alanine, wherein the L-form of the amino acids of the group is preferred. In a specific embodiment of the invention, the compounds of the invention comprise a tripeptide comprising or consisting of one or more amino acids or amino acid residues selected from the group consisting of phenylalanine, and glycine.

In another specific embodiment, the compounds of the invention comprise a tripeptide comprising or consisting of at least two of the amino acid residues selected from the group consisting of phenylalanine, valine, leucine, isoleucine, glycine and alanine.

In another specific embodiment, the compounds of the invention comprise a tripeptide comprising or consisting of at least three of the amino acid residues selected from the group consisting of phenylalanine, valine, leucine, isoleucine, glycine and alanine.

In a specific embodiment of the invention, the tripeptide consists of three alanine residues, or of three phenylalanine residues, or of three leucine residues, or of three isoleucine residues, or of three valine residues.

Thus, in a more specific embodiment, a tripeptide comprises or consists of amino acid residues of a phenylalanine, a glycine and alanine.

In another a more specific embodiment, a tripeptide comprises or consists of amino acid residues of a phenylalanine, a glycine and isoleucine.

In another a more specific embodiment, a tripeptide comprises or consists of amino acid residues of a phenylalanine, a glycine and leucine.

In another more specific embodiment, a tripeptide comprises or consists of amino acid residues of a phenylalanine, a glycine and valine.

In another more specific embodiment, a tripeptide comprises or consists of amino acid residues of a phenylalanine, alanine and isoleucine.

In another more specific embodiment, a tripeptide comprises or consists of amino acid residues of a phenylalanine, alanine and leucine.

In another more specific embodiment, a tripeptide comprises or consists of amino acid residues of a phenylalanine, alanine and valine.

In another more specific embodiment, a tripeptide comprises or consists of amino acid residues of a phenylalanine, isoleucine and leucine.

In another more specific embodiment, a tripeptide comprises or consists of amino acid residues of a phenylalanine, isoleucine and valine.

In another more specific embodiment, a tripeptide comprises or consists of amino acid residues of a phenylalanine, leucine and valine.

In another more specific embodiment, a tripeptide comprises or consists of amino acid residues of a phenylalanine, leucine and valine.

In another a more specific embodiment, a tripeptide comprises or consists of amino acid residues of a glycine, an alanine and an isoleucine.

In another a more specific embodiment, a tripeptide comprises or consists of amino acid residues of a glycine, an alanine and a leucine.

In another a more specific embodiment, a tripeptide comprises or consists of amino acid residues of a glycine, an alanine and a valine.

In another a more specific embodiment, a tripeptide comprises or consists of amino acid residues of a glycine, an isoleucine and leucine.

In another a more specific embodiment, a tripeptide comprises or consists of amino acid residues of a glycine, an isoleucine and valine.

In another a more specific embodiment, a tripeptide comprises or consists of amino acid residues of a glycine, a leucine and valine.

In another a more specific embodiment, a tripeptide comprises or consists of amino acid residues of an isoleucine, a leucine and valine.

As mentioned above, peptide transporters such as hPEPT1 is capable of transporting dipeptides. In a specific embodiment, the compounds of the invention comprise a dipeptide comprising or consisting of at least two of the amino acid residues selected from the group consisting of phenylalanine, valine, leucine, isoleucine, glycine and alanine.

In another specific embodiment, the compounds of the invention comprise a dipeptide consisting of two of the amino acid residues selected from the group consisting of phenylalanine, valine, leucine, isoleucine, glycine and alanine.

In a specific embodiment of the invention, the dipeptide consists of two alanine residues, or of two phenylalanine residues, or of two leucine residues, or of two isoleucine residues, or of two valine residues.

In a specific embodiment, the compounds of the invention comprise a dipeptide comprising a phenylalanine residue.

In another specific embodiment, the compounds of the invention comprise a dipeptide comprising a glycine residue.

Thus, in a more specific embodiment of the invention, the peptide comprises or consists of amino acid residues of a phenylalanine and an alanine.

In another more specific embodiment of the invention, the peptide consists of amino acid residues of a phenylalanine and a glycine.

In another more specific embodiment of the invention, the peptide comprises or consists of amino acid residues of a phenylalanine and an isoleucine.

In another more specific embodiment of the invention, the peptide comprises or consists of amino acid residues of a phenylalanine and a leucine.

In another more specific embodiment of the invention, the peptide comprises or consists of amino acid residues of a phenylalanine and a valine.

In another more specific embodiment of the invention, the peptide comprises or consists of amino acid residues of an alanine and a glycine.

In another more specific embodiment of the invention, the peptide comprises or consists of amino acid residues of an alanine and an isoleucine.

In another more specific embodiment of the invention, the peptide comprises or consists of amino acid residues of an alanine and a leucine.

In another more specific embodiment of the invention, the peptide comprises or consists of amino acid residues of an alanine and a valine.

In another more specific embodiment of the invention, the peptide comprises or consists of amino acid residues of a glycine and an isoleucine.

In another more specific embodiment of the invention, the peptide comprises or consists of amino acid residues of a glycine and a leucine.

In another more specific embodiment of the invention, the peptide comprises or consists of amino acid residues of a glycine and a valine.

In another more specific embodiment of the invention, the peptide comprises or consists of amino acid residues of an isoleucine and a leucine.

In another more specific embodiment of the invention, the peptide comprises or consists of amino acid residues of an isoleucine and a valine.

In another more specific embodiment of the invention, the peptide comprises or consists of amino acid residues of a leucine and a valine.

In a specific embodiment of the invention, one or more of R1, R2, R3 and R4 is an amino acid, amino acid derivative or a peptide linked through a Cα atom of the amino acid, amino acid residue or peptide.

In a specific embodiment of the invention, one or more of R1, R2, R3 and R4 is an amino acid, amino acid residue or a peptide linked through a Cα atom of a glycine residue.

In a preferred embodiment of the invention, one or more of R1, R2, R3 and R4 is an amino acid, amino acid derivative or a peptide linked through a carboxyl group of the amino acid, amino acid residue or peptide.

In a preferred embodiment of the invention, one or more of R1, R2, R3 and R4 is an amino acid or amino acid derivative linked through the backbone carboxyl group of the amino acid or amino acid residue.

In another embodiment of the invention, one or more of R1, R2, R3 and R4 is a phenylalanine or a derivative thereof linked through a benzyl group of the side-chain of the amino acid or amino acid residue.

In another embodiment of the invention, one or more of R1, R2, R3 and R4 is a phenylalanine or a residue thereof linked through a benzyl group of the side chain of the amino acid or amino acid residue.

In a preferred embodiment of the invention, one or more of R1, R2, R3 and R4 is a peptide linked through a carboxyl group of the C-terminal of the peptide backbone.

In a preferred embodiment of the invention, one or more of R1, R2, R3 and R4 is a dipeptide linked through a carboxyl group of the C-terminal of the peptide backbone.

In a preferred embodiment of the invention, one or more of R1, R2, R3 and R4 is a tripeptide linked through a carboxyl group of the C-terminal of the peptide backbone.

The compounds of the invention are useful in the treatment of neurodegenerative diseases and disorders such as Parkinson's disease and/or other conditions for which treatment with a dopamine agonist is therapeutically beneficial. The compounds, being suitable for oral administration have the potential of providing a new treatment paradigm in Parkinson's Disease.

In one embodiment of the invention, the compounds are for use as stand-alone treatment of a neurodegenerative disease or disorder. In another embodiment of the invention, the compounds are to be used in combination with other agents for treatment of PD such as a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

Embodiments of the Invention

In the following, some specific embodiments of the invention are disclosed. The first embodiment is denoted E1, the second embodiment is denoted E2 and so forth E1. A compound according to formula (Id)

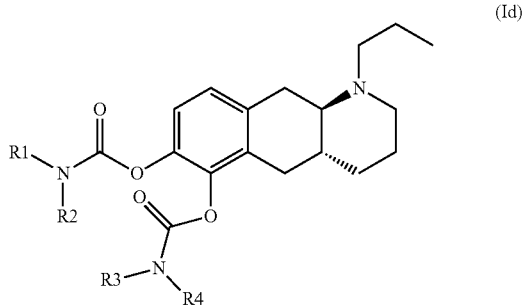

(Id)

wherein
R1, R2, R3 and R4 are each individually selected from H, and $C_{1-6}$ alkyl;
or a pharmaceutically acceptable salt thereof.

E2. The compound or pharmaceutically acceptable salt according to embodiment E1, wherein R1=R3 and R2=R4.

E3. The compound or pharmaceutically acceptable salt according to any of embodiments E1-E2, wherein
R1 and R3 are both H and R2 and R4 are the same $C_{1-6}$ alkyl; or
R1 and R3 are the same $C_{1-6}$ alkyl and R2 and R4 are both H.

E4. The compound or pharmaceutically acceptable salt according to any of embodiments E1-E2, wherein
R1 and R3 are the same $C_{1-6}$ alkyl; and
R2 and R4 are the same $C_{1-6}$ alkyl.

E5. The compound or pharmaceutically acceptable salt according to any of embodiments E1-E2, wherein
R1 and R3 are both H and R2 and R4 are both methyl or both ethyl; or
R1 and R3 are both methyl or both ethyl and R2 and R4 are both H.

E6. The compound or pharmaceutically acceptable salt according to any of embodiments E1-E2, wherein
R1 and R3 are both ethyl or both methyl; and
R2 and R4 are both ethyl or both methyl.

E7. The compound according to embodiment E1, wherein the compound is selected from the group consisting of:
Compound (1): (4aR,10aR)-1-propyl-1,2,3,4,4a,5,10,10a-octahydrobenzo[g]quinoline-6,7-diyl bis(methylcarbamate)
Compound (2): (4aR,10aR)-1-propyl-1,2,3,4,4a,5,10,10a-octahydrobenzo[g]quinoline-6,7-diyl bis(ethylcarbamate); and
Compound (3): (4aR,10aR)-1-propyl-1,2,3,4,4a,5,10,10a-octahydrobenzo[g]quinoline-6,7-diyl bis(dimethylcarbamate);
or a pharmaceutically acceptable salt of any of these compounds.

E8. A compound which is a prodrug of the compound (4aR,10aR)-1-Propyl-1,2,3,4,4a,5,10,10a-octahydro-benzo[g]quinoline-6,7-diol (compound (I)), wherein said prodrug provides a PK profile wherein $C_{max}$ of (4aR,10aR)-1-Propyl-1,2,3,4,4a,5,10,10a-octahydro-benzo[g]quinoline-6,7-diol is between 25 and 200 pg/mL, such as between 50 and 150 pg/mL, such as between 50 and 100 pg/mL when said prodrug is administered orally to a Wistar rat in a dose corresponding to 287 μg/kg of (4aR,10aR)-1-Propyl-1,2,3,4,4a,5,10,10a-octahydro-benzo[g]quinoline-6,7-diol;
or a pharmaceutically acceptable salt of said compound.

E9. The compound or pharmaceutically acceptable salt thereof according to embodiment E8, which is a prodrug of the compound (4aR,10aR)-1-Propyl-1,2,3,4,4a,5,10,10a-octahydro-benzo[g]quinoline-6,7-diol (compound (I)), wherein said prodrug provides a PK profile wherein $AUC_{0-24}$ of (4aR,10aR)-1-Propyl-1,2,3,4,4a,5,10,10a-octahydro-benzo[g]quinoline-6,7-diol is more than 1000 pg*h/mL when said prodrug is administered orally to a Wistar rat in a dose corresponding to 287 μg/kg of (4aR,10aR)-1-Propyl-1,2,3,4,4a,5,10,10a-octahydro-benzo[g]quinoline-6,7-diol.

E10. The compound or pharmaceutically acceptable salt thereof according to any of embodiments E8-E9, wherein said PK profile has been obtained by a PK experiment as described in Example 3 herein.

E11. The compound or pharmaceutically acceptable salt thereof according to any of embodiments E1-E10, for use in therapy.

E12. A compound or pharmaceutically acceptable salt thereof according to any of embodiments E1-E10, for use as a medicament.

E13. The compound or pharmaceutically acceptable salt for use as a medicament according to embodiment E12, wherein said medicament is an oral medicament such as a tablet or a capsule for oral administration.

E14. A pharmaceutical composition comprising a therapeutically effective amount of the compound or pharmaceutically acceptable salt thereof according to any of embodiments E1-E10, and one or more pharmaceutically acceptable excipients.

E15. The pharmaceutical composition according to embodiment E14, wherein said pharmaceutical composition is for oral administration.

E16. The pharmaceutical composition according to any of embodiments E14-E15, wherein said pharmaceutical composition is an oral pharmaceutical composition.

E17. The pharmaceutical composition according to any of embodiments E14-E16, wherein said pharmaceutical composition is a solid oral dosage form.

E18. The pharmaceutical composition according to any of embodiments E14-E17, wherein said pharmaceutical composition is a tablet or a capsule for oral administration.

E19. The pharmaceutical composition according to any of embodiments E14-E18, wherein said pharmaceutical composition further comprises another agent which is useful in the treatment of a neurodegenerative disease or disorder such as Parkinson's disease.

E20. The pharmaceutical composition according to any of embodiments E14-E19, wherein said pharmaceutical composition further comprises a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or an antibody targeting alpha-synuclein, Tau or A-beta protein.

E21. A compound or pharmaceutically acceptable salt thereof according to any of embodiments E1-E10, for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

E22. The compound or pharmaceutically acceptable salt thereof according to any of embodiments E1-E10, for use in the treatment according to embodiment E21, wherein said neurodegenerative disease or disorder is Parkinson's Disease.

E23. The compound or pharmaceutically acceptable salt thereof according to any of embodiments E1-E10, for use in the treatment according to any of embodiments E21-E22, wherein said compound is to be used in combination with another agent which is useful in the treatment of a neurodegenerative disease or disorder such as Parkinson's disease.

E24. The compound or pharmaceutically acceptable salt thereof according to any of embodiments E1-E10, for use in the treatment according to any of embodiments E21-E23, wherein said compound is to be used in combination with a compound selected from the group consisting of L-DOPA, droxidopa, folliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E25. The compound or pharmaceutically acceptable salt thereof according to any of embodiments E1-E10, for use in the treatment according to any of embodiments E21-E24, wherein said treatment is performed by oral administration of said compound.

E26. The compound or pharmaceutically acceptable salt thereof according to any of embodiments E1-E10, for use in the treatment according to any of embodiments E21-E25, wherein said compound is comprised in an oral pharmaceutical composition such as a tablet or a capsule for oral administration.

E27. A method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of a compound or pharmaceutically acceptable salt thereof according to any of embodiments E1-E10, to a patient in need thereof.

E28. The method according to embodiment E27, wherein said neurodegenerative disease or disorder is Parkinson's Disease.

E29. The method according to any of embodiments E27-E28, wherein said compound or pharmaceutically acceptable salt thereof according to any of embodiments E1-E10, is used in combination with another agent which is useful in the treatment of a neurodegenerative disease or disorder such as Parkinson's disease.

E30. The method according to any of embodiments E27-E29, wherein said compound or pharmaceutically acceptable salt thereof according to any of embodiments E1-E10, is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E31. The method according to any of embodiments E27-E30, wherein said administration is performed by the oral route.

E32. The method according to any of embodiments E27-E31, wherein said compound or pharmaceutically acceptable salt thereof according to any of embodiments E1-E10 is comprised in an oral pharmaceutical composition such as a tablet or a capsule for oral administration.

E33. Use of a compound or pharmaceutically acceptable salt thereof according to any of embodiments E1-E10, in the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

E34. The use according to embodiment E33, wherein said neurodegenerative disease or disorder is Parkinson's Disease.

E35. The use according to any of embodiments E33-E34, wherein said medicament is used in combination with another agent which is useful in the treatment of a neurodegenerative disease or disorder such as Parkinson's disease.

E36. The use according to any of embodiments E33-E35, wherein said medicament is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E37. The use according to any of embodiments E33-E36, wherein said medicament is an oral medicament such as a tablet or a capsule for oral administration.

FURTHER EMBODIMENTS OF THE INVENTION

The following section further describes embodiments and aspects of the invention are. The first embodiment is denoted EE1, the second embodiment is denoted EE2 and so forth.

EE1. A compound according to formula (Ie)

(Ie)

wherein Y is selected from H and a carbamoyl group of the formula (CONR1R2) below (CONR1R2)

and wherein X is selected from H and a carbamoyl group of the formula (CONR3R4) below (CONR3R4)

and
wherein Y and X are not both H, and
wherein R1, R2, R3 and R4 are each individually selected from the group consisting of H, $C_{1-6}$ alkyl, an amino acid, an amino acid residue and a peptide;
or a pharmaceutically acceptable salt thereof.

EE2. The compound or pharmaceutically acceptable salt according to embodiment EE1, wherein
Y is a carbamoyl group of the formula (CONR1R2), and
X is H.

EE3. The compound or pharmaceutically acceptable salt according to embodiment EE1, wherein
Y is H, and
X is a carbamoyl group of the formula (CONR3R4).

EE4. The compound or pharmaceutically acceptable salt according to embodiment EE1, wherein
Y is a carbamoyl group of the formula (CONR1R2), and
X is a carbamoyl group of the formula (CONR3R4).

EE5. The compound or pharmaceutically acceptable salt according to any one of embodiments EE1-EE4, wherein at least one of R1, R2, R3, and R4, is an amino acid, an amino acid residue, or a peptide.

EE6. The compound or pharmaceutically acceptable salt according to any one of embodiments EE1-EE5, wherein at least one of R1, R2, R3, and R4, is an amino acid, an amino acid residue, or a peptide, and wherein said amino acid, amino acid residue or peptide is of the L-confirmation.

EE7. The compound or pharmaceutically acceptable salt according to any one of embodiments EE1-EE6, wherein at least one of R1, R2, R3, and R4, is an amino acid, an amino acid residue, or a peptide, and wherein N is connected to an amino acid backbone atom of said amino acid, an amino acid residue, or peptide.

EE8. The compound or pharmaceutically acceptable salt according to any one of embodiments EE1-EE6, wherein at least one of R1, R2, R3, and R4, is an amino acid, an amino acid residue, or a peptide, and wherein N is connected to a Cα atom of said amino acid, amino acid residue or peptide.

EE9. The compound or pharmaceutically acceptable salt according to any one of embodiments EE1-EE6, wherein at least one of R1, R2, R3, and R4, is an amino acid, an amino acid residue, or a peptide, and wherein N is connected to a backbone carbonyl group of said amino acid, amino acid residue, or peptide.

EE10. The compound or pharmaceutically acceptable salt according to any one of embodiments EE1-EE6, wherein at least one of R1, R2, R3, and R4, is an amino acid, an amino acid residue, or a peptide, and wherein N is connected to a side chain atom of said amino acid, an amino acid residue or peptide.

EE11. The compound or pharmaceutically acceptable salt according to any one of embodiments EE1-EE6, wherein at least one of R1, R2, R3, and R4, is an amino acid, an amino acid residue, or a peptide, and wherein N is connected to a Cβ atom of said amino acid, an amino acid residue or peptide.

EE12. The compound or pharmaceutically acceptable salt according to any one of embodiments EE1-EE6, wherein at least one of R1, R2, R3, and R4, is an amino acid, an amino acid residue, or a peptide, and wherein N is connected to a Cγ side chain atom of said amino acid, an amino acid residue or peptide.

EE13. The compound or pharmaceutically acceptable salt according to any one of embodiments EE1-EE6, wherein at least one of R1, R2, R3, and R4, is an amino acid, an amino acid residue, or a peptide, and wherein N is connected to a Cδ side chain atom of said amino acid, an amino acid residue or peptide.

EE14. The compound or pharmaceutically acceptable salt according to any one of embodiments EE1-EE6, wherein at least one of R1, R2, R3, and R4, is an amino acid, an amino acid residue, or a peptide, and wherein N is connected to a Cε side chain atom of said amino acid, an amino acid residue or peptide.

EE15. The compound or pharmaceutically acceptable salt according to any one of embodiments EE1-EE6, wherein at least one of R1, R2, R3, and R4, is an amino acid, an amino acid residue, or a peptide, and wherein N is connected to a Cζ side chain atom of said amino acid, an amino acid residue or peptide.

EE16. The compound or pharmaceutically acceptable salt according to any one of embodiments EE1-EE6, wherein at least one of R1, R2, R3, and R4, is an amino acid, an amino acid residue, or a peptide, and wherein N is connected to a side chain oxygen atom of said amino acid, amino acid residue or peptide.

EE17. The compound or pharmaceutically acceptable salt according to any one of embodiments EE1-EE6, wherein at least one of R1, R2, R3, and R4, is an amino acid, an amino acid residue, or a peptide, and wherein N is connected to a side chain nitrogen atom of said amino acid, amino acid residue or peptide.

EE18. The compound or pharmaceutically acceptable salt according to any one of embodiments EE1-EE6, wherein at least one of R1, R2, R3, and R4, is an amino acid, an amino acid residue, or a peptide, and wherein N is connected to a side chain sulfur atom of said amino acid, amino acid residue or peptide.

EE19. The compound or pharmaceutically acceptable salt according to any one of embodiments EE1-EE18, wherein
R1 and R3 are both H, and
at least one of R2 and R4 is an amino acid, an amino acid residue, or a peptide; or
wherein R2 and R4 are both H, and
at least one of R1 and R3 is an amino acid, an amino acid residue, or a peptide.

EE20. EE23. The compound or pharmaceutically acceptable salt according to any one of embodiments EE1-EE18, wherein
R1 and R3 are both H, and
only one of R2 and R4 is an amino acid, an amino acid residue, or a peptide; or
wherein R2 and R4 are both H, and
only one of R1 and R3 is an amino acid, an amino acid residue, or a peptide.

EE21. compound or pharmaceutically acceptable salt according to any one of embodiments EE1-EE18, wherein
R1 and R3 are both H, and
one of R2 and R4 is an amino acid, an amino acid residue, or a peptide, and
one of R2 and R4 is H; or
wherein R2 and R4 are both H, and
one of R1 and R3 is an amino acid, an amino acid residue, or a peptide, and
one of one of R1 and R3 is H.

EE22. The compound or pharmaceutically acceptable salt according to any one of embodiments EE1-EE21, wherein
R1, R2 and R3 are H, and
R4 is an amino acid, an amino acid residue, or a peptide.

EE23. The compound or pharmaceutically acceptable salt according to any one of embodiments EE1-21, wherein
R1, R2 and R4 are H, and
R3 is an amino acid, an amino acid residue, or a peptide.

EE24. The compound or pharmaceutically acceptable salt according to any one of embodiments EE1-EE21, wherein
R1, R3 and R4 are H, and
R2 is an amino acid, an amino acid residue, or a peptide.

EE25. The compound or pharmaceutically acceptable salt according to any one of embodiments EE1-EE21, wherein
R2, R3 and R4 are H, and
R1 is an amino acid, an amino acid residue, or a peptide.

EE26. The compound or pharmaceutically acceptable salt according to any one of embodiments EE1-EE21, wherein
R1 is an amino acid residue.

EE27. The compound or pharmaceutically acceptable salt according to any one of embodiments EE1-EE26, wherein
R2 is an amino acid residue.

EE28. The compound or pharmaceutically acceptable salt according to any one of embodiments EE1-EE27, wherein
R3 is an amino acid residue.

EE29. The compound or pharmaceutically acceptable salt according to any one of embodiments EE1-EE28, wherein
R4 is an amino acid residue.

EE30. The compound or pharmaceutically acceptable salt according to any one of embodiments EE1-EE21, wherein
R1 and R3 are both H, and wherein at least one of R2 and R4 is an amino acid residue; or wherein
R2 and R4 are both H, and wherein at least one of R1 and R3 is an amino acid residue.

EE31. The compound or pharmaceutically acceptable salt according to any one of embodiments EE1-EE2, EE7-EE21, wherein
R1 and R3 are both H, and wherein one of R2 and R4 is an amino acid residue, and wherein one of R2 and R4 is H; or wherein
R2 and R4 are both H, and wherein one of R1 and R3 is an amino acid residue, and wherein one of R1 and R3 is H;

EE32. The compound or pharmaceutically acceptable salt according to any one of embodiments EE1-EE31, wherein the amino acid is selected from the group consisting of arginine, lysine, aspartic acid, glutamic acid, glutamine, asparagine, histidine, serine, threonine, tyrosine, cysteine, tryptophan, methionine, alanine, isoleucine, leucine, phenylalanine, valine, proline and glycine.

EE33. The compound or pharmaceutically acceptable salt according to any one of embodiments EE1-EE32, wherein the amino acid residue is selected from the group consisting of amino acid residues of arginine, lysine, aspartic acid, glutamic acid, glutamine, asparagine, histidine, serine, threonine, tyrosine, cysteine, tryptophan, methionine, alanine, isoleucine, leucine, phenylalanine, valine, proline and glycine.

EE34. The compound or pharmaceutically acceptable salt according to any one of embodiments EE1-EE33, wherein the amino acid residue is selected from the group consisting of phenylalanine, valine, leucine, isoleucine, glycine and alanine.

EE35. The compound or pharmaceutically acceptable salt according to any one of embodiments EE1-EE34, wherein the amino acid residue is selected from the group consisting of phenylalanine, and glycine.

EE36. The compound or pharmaceutically acceptable salt according to any one of embodiments EE1-EE25, wherein
R1 and R3 are both H, and wherein at least one of R2 and R4 is a peptide; or wherein
R2 and R4 are both H, and wherein at least one of R1 and R3 is a peptide.

EE37. The compound or pharmaceutically acceptable salt according to any one of embodiments EE1-EE25, wherein
R1 and R3 are both H, and wherein one of R2 and R4 is a peptide, and wherein one of R2 and R4 is H; or wherein
R2 and R4 are both H, and wherein one of R1 and R3 is a peptide, and wherein one of R1 and R3 is H.

EE38. The compound or pharmaceutically acceptable salt according to any one of embodiments EE1-EE25, wherein
R2, R3 and R4 are H, and
R1 is a peptide.

EE39. The compound or pharmaceutically acceptable salt according to any one of embodiments EE1-EE25, wherein
R1, R3 and R4 are H, and
R2 is a peptide.

EE40. The compound or pharmaceutically acceptable salt according to any one of embodiments EE1-EE25, wherein
R1, R2 and R4 are H, and
R3 is a peptide.

EE41. The compound or pharmaceutically acceptable salt according to any one of embodiments EE1-EE25, wherein
R1, R2 and R3 are H, and
R4 is a peptide.

EE42. The compound or pharmaceutically acceptable salt according to any one of embodiments EE1-EE25, and EE36-EE41, wherein the peptide is a dipeptide, a tripeptide, or a derivative of a dipeptide or tripeptide.

EE43. The compound or pharmaceutically acceptable salt according to any one of embodiments EE1-EE25, and EE36-EE42, wherein the peptide comprises two or more amino acid residues selected from the group consisting of arginine, lysine, aspartic acid, glutamic acid, glutamine, asparagine, histidine, serine, threonine, tyrosine, cysteine, tryptophan, methionine, alanine, isoleucine, leucine, phenylalanine, valine, proline and glycine residues.

EE44. The compound or pharmaceutically acceptable salt according to any one of embodiments EE1-EE25, and EE36-EE43, wherein the peptide comprises or consists of two or more amino acids selected from the group consisting of phenylalanine, valine, leucine, isoleucine, glycine and alanine.

EE45. The compound or pharmaceutically acceptable salt according to any one of embodiments EE1-EE25, and EE36-EE44, wherein the peptide comprises or consists of two or more L-amino acids.

EE46. The compound or pharmaceutically acceptable salt according to any one of embodiments EE1-EE25, and EE36-EE45, wherein the peptide is a dipeptide.

EE47. The compound or pharmaceutically acceptable salt according to any one of embodiments EE1-EE2, and EE36-EE46, wherein the peptide is a tripeptide.

EE48. The compound or pharmaceutically acceptable salt according to any one of embodiments EE1-EE25, and EE36-EE47, wherein the peptide comprises one or more amino acid residues selected from the group consisting of phenylalanine and glycine.

EE49. The compound or pharmaceutically acceptable salt according to any one of embodiments EE1-EE25, and EE36-EE48, wherein the peptide is a dipeptide comprising one or more amino acid residues selected from the group consisting of phenylalanine and glycine.

EE50. The compound or pharmaceutically acceptable salt according to any one of embodiments EE1-EE35, wherein one of R1, R2, R3 and R4 is a glycine residue.

EE51. The compound or pharmaceutically acceptable salt according to any one of embodiments EE1-EE35, and EE50 wherein
one of R1, R2, R3 and R4 is a glycine residue, and three of R1, R2, R3 and R4 is H.

EE52. The compound or pharmaceutically acceptable salt according to any one of embodiments EE1-EE35, and EE50-EE51 wherein
one of R1, R2, R3 and R4 is CH2COOH.

EE53. The compound or pharmaceutically acceptable salt according to any one of embodiments EE1-EE35, and EE50-EE52, wherein one of R1, R2, R3 and R4 is CH2COOH, and three of R1, R2, R3 and R4 is H.

EE54. The compound or pharmaceutically acceptable salt according to any one of embodiments EE1-EE35, EE50 and EE52 wherein
one of R1, R2, R3 and R4 is a phenyl alanine residue.

EE55. The compound or pharmaceutically acceptable salt according to any one of embodiments EE1-EE35, and EE54 wherein
one of R1, R2, R3 and R4 is a phenyl alanine residue, and three of R1, R2, R3 and R4 is H.

EE56. The compound or pharmaceutically acceptable salt according to any one of embodiments EE1, EE2 and EE4, wherein
R1 is H and R2 is $C_{1-6}$ alkyl; or
R1 is $C_{1-6}$ alkyl and R2 is H.

EE57. The compound or pharmaceutically acceptable salt according to any one of embodiments EE1, EE2 and EE4, wherein R1 and R2 are the same $C_{1-6}$ alkyl.

EE58. The compound or pharmaceutically acceptable salt according to any one of embodiments EE1, EE2 and EE4, wherein
R1 is H and R2 is methyl or ethyl; or
R1 is methyl or ethyl and R2 is H.

EE59. The compound or pharmaceutically acceptable salt according to any one of embodiments EE1, EE2 and EE4, wherein R1 and R2 are independently selected from methyl and ethyl.

EE60. The compound or pharmaceutically acceptable salt according to any one of embodiments EE1, EE2 and EE4, wherein R1 and R2 are both methyl.

EE61. The compound or pharmaceutically acceptable salt according to any one of embodiments EE1, EE2 and EE4, wherein R1 and R2 are both ethyl.

EE62. The compound or pharmaceutically acceptable salt according to any one of embodiments EE1, EE3 and EE4, wherein
R3 is H and R4 is $C_{1-6}$ alkyl; or
R3 is $C_{1-6}$ alkyl and R4 is H.

EE63. The compound or pharmaceutically acceptable salt according to any one of embodiments EE1, EE3 and EE4, wherein R3 and R4 are the same $C_{1-6}$ alkyl.

EE64. The compound or pharmaceutically acceptable salt according to any one of embodiments EE1, EE3 and EE4, wherein
R3 is H and R4 is methyl or ethyl; or
R3 is methyl or ethyl and R4 is H.

EE65. The compound or pharmaceutically acceptable salt according to any one of embodiments EE1, EE3 and EE4, wherein R3 and R4 are independently selected from methyl and ethyl.

EE66. The compound or pharmaceutically acceptable salt according to any one of embodiments EE1, EE3 and EE4, wherein R3 and R4 are both methyl.

EE67. The compound or pharmaceutically acceptable salt according to any one of embodiments EE1, EE3 and EE4, wherein R3 and R4 are both ethyl.

EE68. The compound or pharmaceutically acceptable salt according to embodiment EE1 and EE4, wherein said compound is of the formula (Id) below (Id)

wherein R1, R2, R3 and R4 are each individually selected from the group consisting of H, $C_{1-6}$ alkyl, an amino acid, an amino acid residue and a peptide;
or a pharmaceutically acceptable salt thereof.

EE69. The compound or pharmaceutically acceptable salt according to embodiment EE68, wherein R1, R2, R3 and R4 are each individually selected from the group consisting of H, linear $C_{1-6}$ alkyl, an amino acid, an amino acid residue and a peptide.

EE70. The compound or pharmaceutically acceptable salt according to embodiments EE68-EE69, wherein
R1=R3 and R2=R4.

EE71. The compound or pharmaceutically acceptable salt according to embodiments EE68-EE70, wherein
R1 and R3 are both H and R2 and R4 are the same $C_{1-6}$ alkyl; or
R1 and R3 are the same $C_{1-6}$ alkyl and R2 and R4 are both H.

EE72. The compound or pharmaceutically acceptable salt according to embodiments EE68-EE71, wherein
R1 and R3 are the same $C_{1-6}$ alkyl; and
R2 and R4 are the same $C_{1-6}$ alkyl.

EE73. The compound or pharmaceutically acceptable salt according to embodiments EE68-EE72, wherein
R1 and R3 are the same linear $C_{1-6}$ alkyl; and
R2 and R4 are the same linear $C_{1-6}$ alkyl.

EE74. The compound or pharmaceutically acceptable salt according to embodiments EE68-EE71, wherein
R1 and R3 are both H and R2 and R4 are both methyl or both ethyl; or
R1 and R3 are both methyl or both ethyl and R2 and R4 are both H.

EE75. The compound or pharmaceutically acceptable salt according to embodiments EE68-EE73, wherein
R1 and R3 are both ethyl or both methyl; and R2 and R4 are both ethyl or both methyl.

EE76. The compound according to embodiment EE1, wherein the compound is selected from the group consisting of:
Compound (1): (4aR,10aR)-1-propyl-1,2,3,4,4a,5,10,10a-octahydrobenzo[g]quinoline-6,7-diyl bis(methylcarbamate)
Compound (2): (4aR,10aR)-1-propyl-1,2,3,4,4a,5,10,10a-octahydrobenzo[g]quinoline-6,7-diyl bis(ethylcarbamate); and
Compound (3): (4aR,10aR)-1-propyl-1,2,3,4,4a,5,10,10a-octahydrobenzo[g]quinoline-6,7-diyl bis(dimethylcarbamate);
Compound (4): ((((4aR,10aR)-7-hydroxy-1-propyl-1,2,3,4,4a,5,10,10a-octahydrobenzo[g]quinolin-6-yl)oxy)carbonyl)glycine;
Compound (5): ((((4aR,10aR)-6-hydroxy-1-propyl-1,2,3,4,4a,5,10,10a-octahydrobenzo[g]quinolin-7-yl)oxy)carbonyl)glycine;
Compound (6): (S)-2-amino-3-(3-(((((4aR,10aR)-7-hydroxy-1-propyl-1,2,3,4,4a,5,10,10a-octahydrobenzo[g]quinolin-6-yl)oxy)carbonyl)amino)phenyl)propanoic acid
and a pharmaceutically acceptable salt of any of these compounds.

EE77. The compound according to embodiment EE1, wherein the compound is selected from the group consisting of:
Compound (1): (4aR,10aR)-1-propyl-1,2,3,4,4a,5,10,10a-octahydrobenzo[g]quinoline-6,7-diyl bis(methylcarbamate)
Compound (2): (4aR,10aR)-1-propyl-1,2,3,4,4a,5,10,10a-octahydrobenzo[g]quinoline-6,7-diyl bis(ethylcarbamate); and
Compound (3): (4aR,10aR)-1-propyl-1,2,3,4,4a,5,10,10a-octahydrobenzo[g]quinoline-6,7-diyl bis(dimethylcarbamate);
and a pharmaceutically acceptable salt of any of these compounds.

EE78. The compound or pharmaceutically acceptable salt thereof according to any one of embodiments EE1-EE77, for use in therapy.

EE79. A compound or pharmaceutically acceptable salt thereof according to any one of embodiments EE1-EE77, for use as a medicament.

EE80. The compound or pharmaceutically acceptable salt for use as a medicament according to EE79, wherein said medicament is an oral medicament such as a tablet or a capsule for oral administration.

EE81. A pharmaceutical composition comprising a therapeutically effective amount of the compound or pharmaceutically acceptable salt thereof according to any one of embodiments EE1-EE77, and one or more pharmaceutically acceptable excipients.

EE82. The pharmaceutical composition according to embodiment EE81, wherein said pharmaceutical composition is for oral administration.

EE83. The pharmaceutical composition according to any one of embodiments EE81-EE82, wherein said pharmaceutical composition is an oral pharmaceutical composition.

EE84. The pharmaceutical composition according to any one of embodiments EE81-EE83, wherein said pharmaceutical composition is a solid oral dosage form.

EE85. The pharmaceutical composition according to any one of embodiments EE81-EE84, wherein said pharmaceutical composition is a tablet or a capsule for oral administration.

EE86. The pharmaceutical composition according to any one of embodiments EE81-EE85, wherein said pharmaceutical composition further comprises another agent which is useful in the treatment of a neurodegenerative disease or disorder such as Parkinson's disease.

EE87. The pharmaceutical composition according to any one of embodiments EE81-EE86, wherein said pharmaceutical composition further comprises a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or an antibody targeting alpha-synuclein, Tau or A-beta protein.

EE88. A compound or pharmaceutically acceptable salt thereof according to any one of embodiments EE1-EE77, for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

EE89. The compound or pharmaceutically acceptable salt thereof according to any one of embodiments EE1-EE77, for use in the treatment according to embodiment EE88, wherein said neurodegenerative disease or disorder is Parkinson's Disease.

EE90. The compound or pharmaceutically acceptable salt thereof according to any one of embodiments EE1-EE77, for use in the treatment according to any one of embodiments EE88-EE89, wherein said compound is to be used in combination with another agent which is useful in the treatment of a neurodegenerative disease or disorder such as Parkinson's disease.

EE91. The compound or pharmaceutically acceptable salt thereof according to any one of embodiments EE1-EE77, for use in the treatment according to any one of embodiments EE88-EE90, wherein said compound is to be used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

EE92. The compound or pharmaceutically acceptable salt thereof according to any one of embodiments EE1-EE77, for use in the treatment according to any one of embodiments EE88-EE90, wherein said treatment is performed by oral administration of said compound.

EE93. The compound or pharmaceutically acceptable salt thereof according to any one of embodiments EE1-EE77, for use in the treatment according to any one of embodiments EE88-EE92, wherein said compound is comprised in an oral pharmaceutical composition such as a tablet or a capsule for oral administration.

EE94. A method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of a compound or pharmaceutically acceptable salt thereof according to any one of embodiments EE1-EE77, to a patient in need thereof.

EE95. The method according to embodiment EE94, wherein said neurodegenerative disease or disorder is Parkinson's Disease.

EE96. The method according to any one of embodiments EE94-EE95, wherein said compound or pharmaceutically acceptable salt thereof according to any one of embodiments EE1-EE77, is used in combination with another agent which is useful in the treatment of a neurodegenerative disease or disorder such as Parkinson's disease.

EE97. The method according to any one of embodiments EE94-EE96, wherein said compound or pharmaceutically acceptable salt thereof according to any one of embodiments EE1-EE77, is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

EE98. The method according to any one of embodiments EE94-EE97, wherein said administration is performed by the oral route.

EE99. The method according to any one of embodiments EE94-EE98, wherein said compound or pharmaceutically acceptable salt thereof according to any one of embodiments EE1-EE77 is comprised in an oral pharmaceutical composition such as a tablet or a capsule for oral administration.

EE100. Use of a compound or pharmaceutically acceptable salt thereof according to any one of embodiments EE1-EE77, in the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

EE101. The use according to embodiment EE100, wherein said neurodegenerative disease or disorder is Parkinson's Disease.

EE102. The use according to any one of embodiments EE100-EE101, wherein said medicament is used in combination with another agent which is useful in the treatment of a neurodegenerative disease or disorder such as Parkinson's disease.

EE103. The use according to any one of embodiments EE100-EE102, wherein said medicament is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

EE104. The use according to any one of embodiments EE100-EE103, wherein said medicament is an oral medicament such as a tablet or a capsule for oral administration.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only and should not be construed as limiting the invention in any way.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (including "for instance", "for example", "e.g.", and "as such") in the present specification is intended merely to better illuminate the invention and does not pose a limitation on the scope of invention unless otherwise indicated.

It should be understood that the various aspects, embodiments, implementations and features of the invention mentioned herein may be claimed separately, or in any combination.

The present invention includes all modifications and equivalents of the subject-matter recited in the claims appended hereto, as permitted by applicable law.

Compounds of the Invention

TABLE 2

Exemplified compounds of the invention

| Example | Compound |
| --- | --- |
| Compound (1) | (4aR,10aR)-1-propyl-1,2,3,4,4a,5,10,10a-octahydrobenzo[g]quinoline-6,7-diyl bis(methylcarbamate) |
| Compound (2) | (4aR,10aR)-1-propyl-1,2,3,4,4a,5,10,10a-octahydrobenzo[g]quinoline-6,7-diyl bis(ethylcarbamate) |
| Compound (3) | (4aR,10aR)-1-propyl-1,2,3,4,4a,5,10,10a-octahydrobenzo[g]quinoline-6,7-diyl bis(dimethylcarbamate) |
| Compound (4) | (W4aR,10aR)-7-hydroxy-1-propyl-1,2,3,4,4a,5,10,10a-octahydrobenzo[g]quinolin-6-yl)oxy)carbonyl)glycine |
| Compound (5) | (W4aR,10aR)-6-hydroxy-1-propyl-1,2,3,4,4a,5,10,10a-octahydrobenzo[g]quinolin-7-yl)oxy)carbonyl)glycine |
| Compound (6) | (S)-2-amino-3-(3-(((((4aR,10aR)-7-hydroxy-1-propyl-1,2,3,4,4a,5,10,10a-octahydrobenzo[g]quinolin-6-yl)oxy)carbonyl)amino)phenyl)propanoic acid |

Experimental Section

Preparation of the Compounds of the Invention

The compounds of formula (Id) may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-XII" (published with Wiley-Interscience). Preferred methods include, but are not limited to, those described below.

The schemes are representative of methods useful in synthesizing the compounds of the present invention. They are not intended to constrain the scope of the invention in any way.

List of Abbreviations for Chemical Compounds $BF_3$—$OEt_2$: Boron trifluoride diethyl etherate
BnBr: Benzyl bromide
BnCl: Benzyl chloride
DCM: Dichloromethane
DMF: Dimethylformamide
ee: Enantiomeric excess
EtOAc: Ethyl acetate
MeCN: Acetonitrile
MeOH: Methanol
MeI: Methyl iodide
MOM-CI: Chloromethyl methyl ether
Pd/C: Palladium on carbon
Pyridine-HF: Pyridine hydrogenfluoride
TBAF: Tetrabutylamommonium fluoride
TFA: Trifluoroacetic acid
TMS-I: Trimethylsilyl iodide LC-MS Methods Analytical LC-MS data were obtained using the methods identified below, unless otherwise described in details in the experimental protocols below.

Method 550:

LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC BEH C18 1.7 μm; 2.1×50 mm operating at 60° C. with 1.2 ml/min of a binary gradient consisting of water+0.05% trifluoroacetic acid (A) and acetonitrile/water (95:5)+0.05% trifluoroacetic acid.

Gradient:

| | |
| --- | --- |
| 0.00 min | 10% B |
| 1.00 min | 100% B |
| 1.01 min | 10% B |
| 1.15 min | 10% B |

Total run time: 1.15 minutes

Method 10-90AB (Shimadzu LC-20AD&MS 2010):

| | |
| --- | --- |
| Method name: | 10-90AB |
| Instrument: | Shimadzu LC-20AD & MS 2020 |
| MS Mode: | Positive |
| MS Range: | 100-1000 |
| CDL Temp | 250° C. |
| Heat block Temp | 28° C. |
| Nebulizing gas flow | 1.5 L/min |

LC-conditions: the column was a Luna-C18(2) 2.0*30 mm, (3 micrometer particles) operated at 40° C. with 0.8 mL/min (0.01-1.51 min) and 1.2 mL/min (1.52-2.00 min) of a gradient of water+0.037% TFA (A) and MeCN+0.018% TFA (B).

Gradient:

| | |
| --- | --- |
| 0.01 min | 10% B |
| 0.01-1.15 min | 10-90% B |
| 1.15-1.65 min | 90% B |
| 1.65-1.66 min | 90-10% B |
| 1.66-2.00 min | 10% B |
| Total run time: 2.00 min | |

LC-MS Method B:

LC-MS were run on Agilent 1260 HPLC consisting of column comp, Binary pump, Hip sample, and Single Q-MS equipped with ESI-source operating in positive ion mode.

LC-conditions: Column: Inertsustain AQ-C18 HP 3.0 μm; 3.0×50 mm operating at 35° C. with 1.2 ml/min of a binary gradient consisting of water+0.05% trifluoroacetic acid (A) and acetonitrile+0.05% trifluoroacetic acid (B).
Gradient:

| | |
|---|---|
| 0.00 min | 0% B |
| 3.00 min | 95% B |
| 4.00 min | 95% B |

Total run time: 4.0 minutes

General Schemes for Preparing Compounds (1) to (3) of the Invention (4aR,10aR)-1-Propyl-1,2,3,4,4a,5,10,10a-octahydrobenzo[g]quinoline-6,7-diol hydrochloride [Compound (I)] which can for example be prepared as disclosed in WO 2009/026934 was used as a substrate to synthesize compounds (1)-(3) of the invention according to the scheme below.

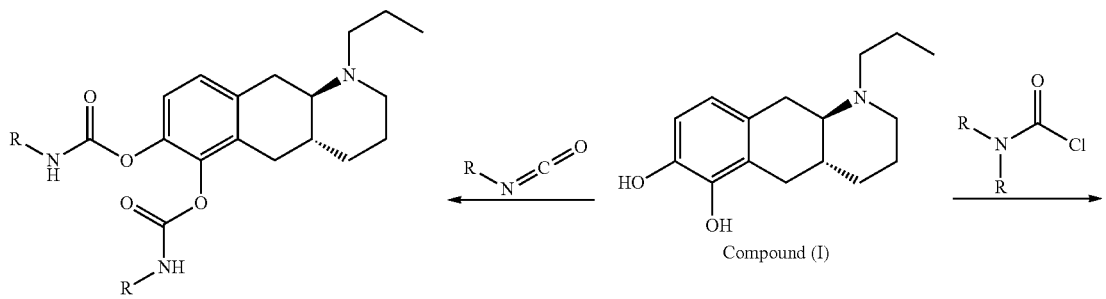

Compound (I)

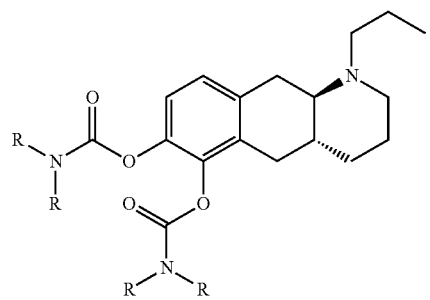

Prodrugs bearing two identical carbamate groups can be prepared by treatment of compound (I) with a carbamoylchloride such as N,N-dimethylcarbamoylchloride in the presence of a base such as triethyl amine or $K_2CO_3$ as described for (4aR,10aR)-1-propyl-1,2,3,4,4a,5,10,10a-octahydrobenzo[g]quinoline-6,7-diyl bis(dimethylcarbamate). Compound (I) can be reacted with an isocyanate such as ethyl isocyanate and a suitable base such as triethyl amine or $K_2OC_3$ as described for (4aR,10aR)-1-propyl-1,2,3,4,4a,5,10,10a-octahydrobenzo[g]quinoline-6,7-diyl bis(ethylcarbamate).

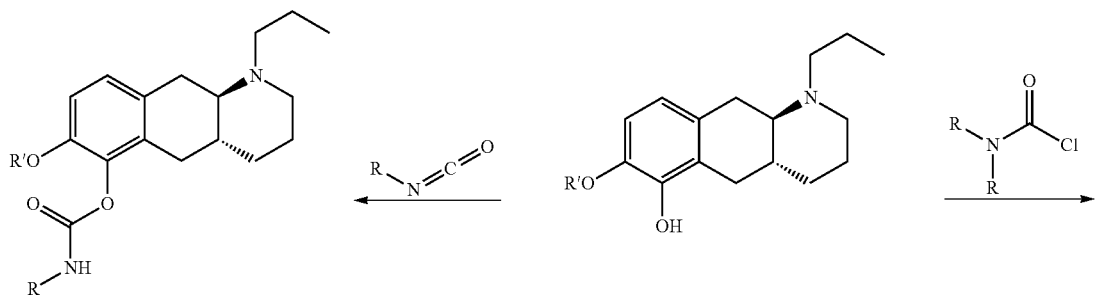

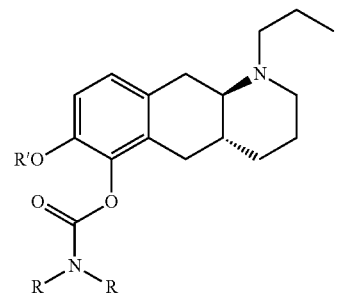

R' = Me: (4aR, 10aR)-7-methoxy-1-propyl-1,2,3,4,4a,5,10,10a-octahydrobenzo[g]quinolin-6-ol R' = Bn: (4aR, 10aR)-7-(benzyloxy)-1-propyl-1,2,3,4,4a,5,10,10a-octahydrobenzo[g]quinolin-6-ol Prodrugs with only one of the catechol hydroxyl groups alkylated can be prepared from compounds like (4aR,10aR)-7-(benzyloxy)-1-propyl-1,2,3,4,4a,5,10,10a-octahydrobenzo[g]quinolin-6-ol (compound A2) or (4aR,10aR)-7-methoxy-1-propyl-1,2,3,4,4a,5,10,10a-octahydrobenzo[g]quinolin-6-ol (compound A6) by treatment with either a carbamoylchloride or a isocyanate in the presence or absence of a suitable base like triethyl amine, diethylisopropyl amine, or potassium carbonate. In these reactions, compounds A2 and A6 can be used in their free form or as the acid addition salt such as the hydrogen iodide (A2-HI), hydrogen bromide, or hydrogen chloride salt. The synthesis of the two precursors is described herein. The opposite regioisomers can be prepared from (4aR,10aR)-6-methoxy-1-propyl-1,2,3,4,4a,5,10,10a-octahydrobenzo[g]quinolin-7-ol or (4aR,10aR)-6-benzyloxy-1-propyl-1,2,3,4,4a,5,10,10a-octahydrobenzo[g]quinolin-7-ol in a similar manner.

Treatment of compound (I) with BnCl and a base such as triethyl amine or K$_2$CO$_3$ will afford a mixture of (4aR, 10aR)-6-(benzyloxy)-1-propyl-1,2,3,4,4a,5,10,10a-octahydrobenzo[g]quinolin-7-ol and (4aR,10aR)-7-(benzyloxy)-1-propyl-1,2,3,4,4a,5,10,10a-octahydrobenzo[g]quinolin-6-ol; these regioisomers can be separated. Using MeI instead of BnCl will afford the corresponding mixture of methyl ethers, which can be separated.

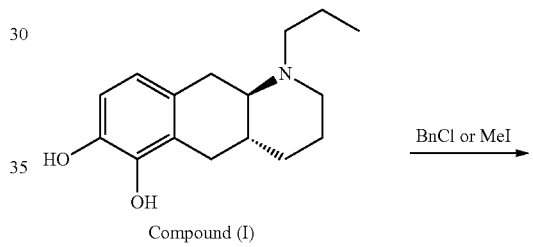

Compound (I)

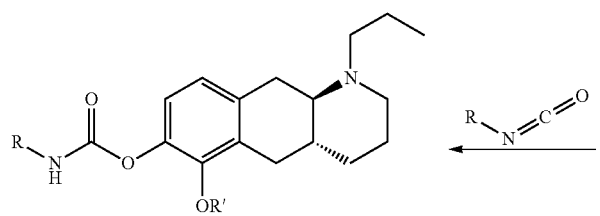

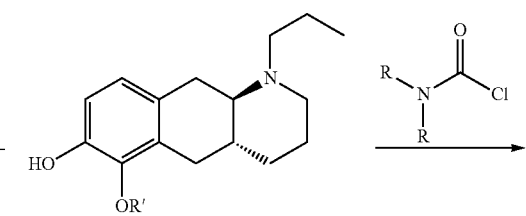

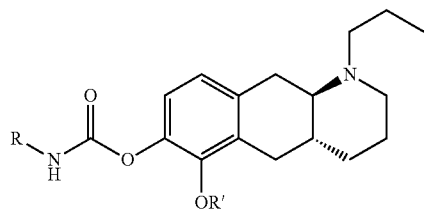

R' = Me: (4aR, 10aR)-6-methoxy-1-propyl-1,2,3,4,4a,5,10,10a-octahydrobenzo[g]quinolin-7-ol R' = Bn: (4aR, 10aR)-6-(benzyloxy)-1-propyl-1,2,3,4,4a,5,10,10a-octahydrobenzo[g]quinolin-7-ol

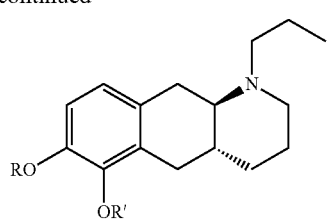

R = H, R' = Bn: (4aR, 10aR)-6-(benzyloxy)-1-propyl-1,2,3,4,4a,5,10,10a-octahydrobenzo[g]quinolin-7-ol R = Bn, R' = H: (4aR, 10aR)-7-(benzyloxy)-1-propyl-1,2,3,4,4a,5,10,10a-octahydrobenzo[g]quinolin-6-ol R = H, R' = Me: (4aR, 10aR)-6-methoxy-1-propyl-1,2,3,4,4a,5,10,10a-octohydrobenzo[g]quinolin-7-ol R = Me, R' = H: (4aR, 10aR)-7-methoxy-1-propyl-1,2,3,4,4a,5,10,10a-octahydrobenzo[g]quinolin-6-ol Selective routes to (4aR,10aR)-7-(benzyloxy)-1-propyl-1,2,3,4,4a,5,10,10a-octahydrobenzo[g]quinolin-6-ol and (4aR,10aR)-7-methoxy-1-propyl-1,2,3,4,4a,5,10,10a-octahydrobenzo[g]quinolin-6-ol are provided herein.

(4aR,10aR)-6-Methoxy-1-propyl-1,2,3,4,4a,5,10,10a-octahydrobenzo[g]quinolin-7-ol can be prepared from (4aR,10aR)-7-(benzyloxy)-1-propyl-1,2,3,4,4a,5,10,10a-octahydrobenzo[g]quinolin-6-ol by methylation followed by debenzylation or by using the MOM-based protective group strategy used in the synthesis of (4aR,10aR)-7-methoxy-1-propyl-1,2,3,4,4a,5,10,10a-octahydrobenzo[g]quinolin-6-ol.

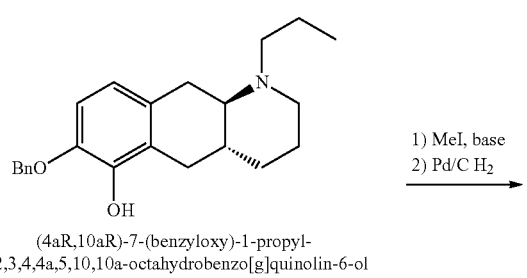

An alternative route to (4aR,10aR)-6-(benzyloxy)-1-propyl-1,2,3,4,4a,5,10,10a-octahydrobenzo[g]quinolin-7-ol can be based on treatment of (4aR,10aR)-1-propyl-7-((triisopropylsilyl)oxy)-1,2,3,4,4a,5,10,10a-octahydrobenzo[g]quinolin-6-ol with benzyl 2,2,2-trichloroacetimidate in the presence of a suitable Lewis acid like BF₃—OEt₂ followed by cleavage of the silyl protection group with KOH, TBAF, or pyridine-HF.

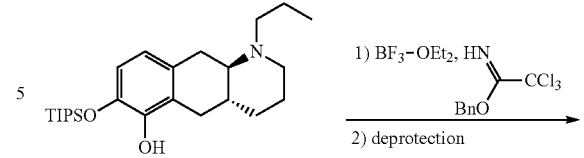

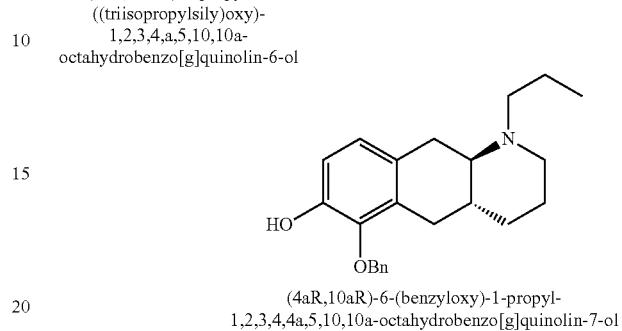

Intermediates of the Invention

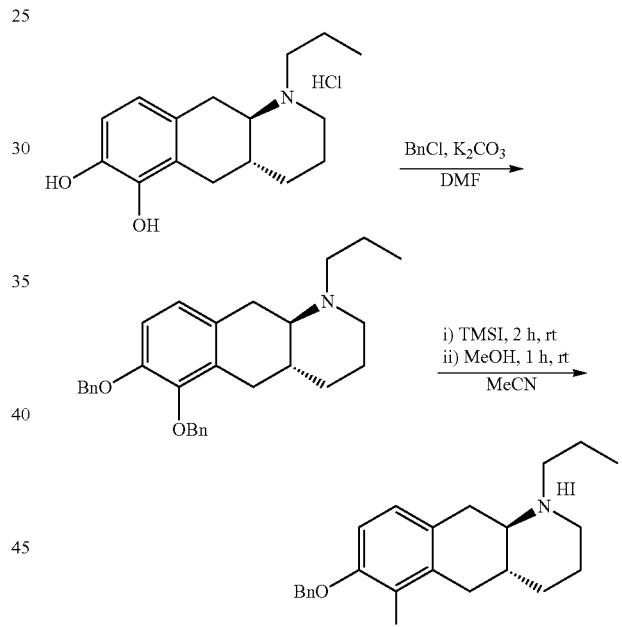

A1: (4aR,10aR)-6,7-bis(benzyloxy)-1-propyl-1,2,3,4,4a,5,10,10a-octahydrobenzo[g]quinoline A one-necked 1 L round-bottom flask with a magnetic stir bar was charged with the hydrochloride salt of Compound (I) (10.75 g) and K₂CO₃ (17.5 g). The flask was evacuated and back-filled with nitrogen followed by the introduction of dry DMF (107 mL). Subsequently, benzyl chloride (8.55 mL) was added and the mixture was stirred at room temperature for 18 hours, then warmed to 100° C. for 5 hours and then cooled to room temperature and stirred for additional 19 hours. Subsequently, additional K₂CO₃ (7.48 g) and benzyl chloride (6.29 mL) were added and the mixture was stirred for 5 hours at 100° C. Then, the mixture was cooled to room temperature and water (500 mL) and heptane (250 mL) were added. The aqueous phase was extracted with heptane (3×100 mL) and the combined organic phases were washed with brine (100 mL), dried over sodium sulfate, filtered, and concentrated to afford the title compound (14.6 g).

A2-HI: (4aR,10aR)-7-(benzyloxy)-1-propyl-1,2,3,4,4a,5,10,10a-octahydrobenzo[g]quinolin-6-ol Hydrogen Iodide A 1 L one-necked round-bottom flask was charged with a magnetic stir bar and (4aR,10aR)-6,7-bis(benzyloxy)-1-propyl-1,2,3,4,4a,5,10,10a-octahydrobenzo[g]quinoline (11.9 g). A rubber stopper was placed in the flask and the flask was evacuated and back-filled with nitrogen. MeCN (180 mL) was added and the mixture was stirred until all starting material was dissolved. TMS-I (10.0 mL) was added and the mixture was stirred at room temperature for 2 hours. Then, MeOH (5.5 mL) was added and the mixture was stirred for 1 hour. Subsequently, 1:15 (v/v) isopropyl acetate/heptane (160 mL) was added and the mixture was cooled (ice-bath) and stirred for 60 minutes. The precipitate was filtered off and washed with 1:15 (v/v) isopropyl acetate/heptane (1×50 mL). The solid was dried to afford the title compound (7.6 g).

LCMS (method 550), Retention time=0.55 minutes, [M+H]$^+$=352.5.

$^1$H NMR (600 MHz, CDCl$_3$) δ 10.42 (bs, 1H), 7.43-7.33 (m, 4H), 7.26 (d, J=1.0 Hz, 1H), 6.78 (d, J=8.3 Hz, 1H), 6.58 (d, J=8.3 Hz, 1H), 5.72 (s, 1H), 5.08 (s, 2H), 3.71 (dd, J=11.70, 15.0 Hz, 1H), 3.58 (d, J=11.70, 1H), 3.25-3.11 (m, 4H), 2.94-2.86 (m, 1H), 2.77-2.57 (m, 2H), 2.26 (dd, J=11.70 Hz, 17.0 Hz 1H), 2.19 (d, J=13.80, 1H), 2.01-1.92 (m, 2H), 1.80-1.69 (m, 1H), 1.56-1.53 (m, 1H), 1.39 (qd, J=3.60 Hz, 13.30 Hz, 1H), 1.06 (t, J=7.2 Hz, 3H).

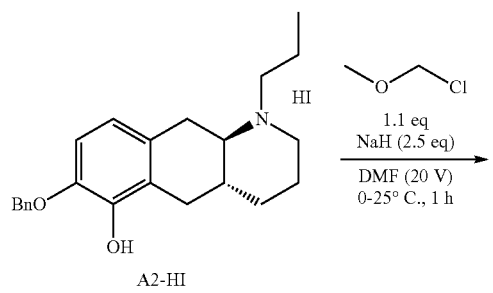

A2-HI

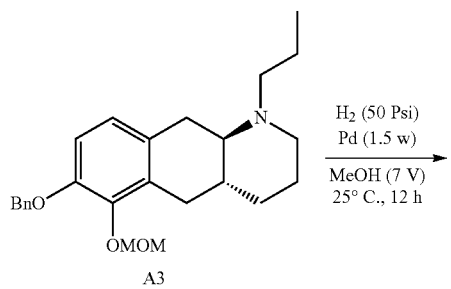

A3

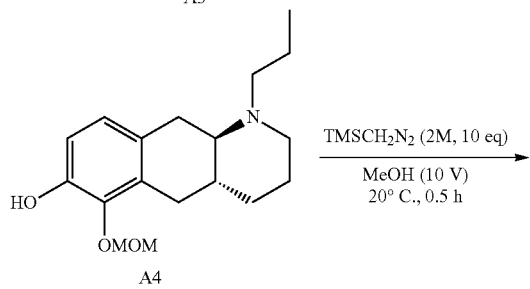

A4

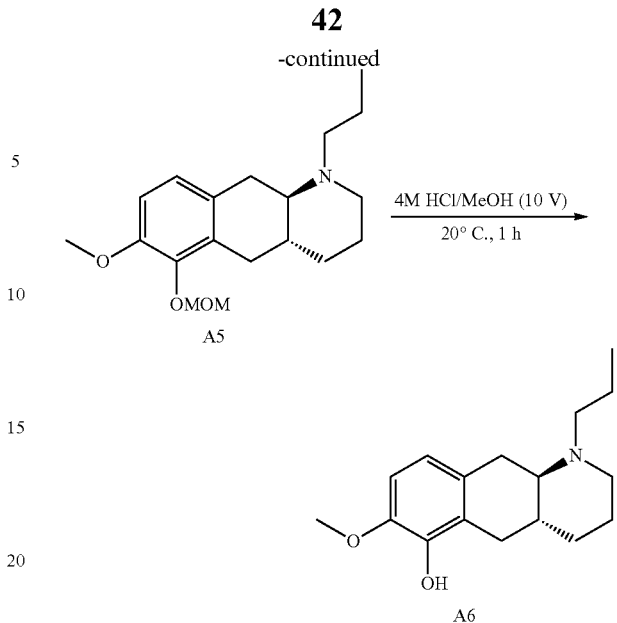

A5

A6

A3: (4aR,10aR)-7-(benzyloxy)-6-(methoxymethoxy)-1-propyl-1,2,3,4,4a,5,10,10a-octahydrobenzo[g]quinoline To a mixture of (4aR,10aR)-7-(benzyloxy)-1-propyl-1,2,3,4,4a,5,10,10a-octahydrobenzo[g]quinolin-6-ol (20 g) in DMF (400 mL) was added NaH (4.17 g, 60% dispersion) slowly at 0° C. The mixture was stirred at 0° C. for 30 minutes. Then MOMCl (3.5 mL) was added drop-wise at 0° C. The mixture was stirred at room temperature for 1 hour. The reaction mixture was poured into water (400 mL) and stirred for 20 minutes. The aqueous phase was extracted with EtOAc (300 mL×3). The combined organic layers were washed with brine (500 mL), dried over sodium sulfate, filtered, and concentrated to afford the title compound (20 g).

LCMS (method 10-90AB), Retention time=0.90 minutes, [M+H]$^+$=396.3.

A4: (4aR,10aR)-6-(methoxymethoxy)-1-propyl-1,2,3,4,4a,5,10,10a-octahydrobenzo[g]quinolin-7-ol To a solution of (4aR,10aR)-7-(benzyloxy)-6-(methoxymethoxy)-1-propyl-1,2,3,4,4a,5,10,10a-octahydrobenzo[g]quinoline (20 g) in MeOH (140 mL) was added 10% Pd/C (30 g) under N$_2$. The suspension was degassed and purged with H$_2$. The mixture was stirred under H$_2$ (50 psi) at 25° C. for 12 hours. The reaction mixture was filtered through a pad of celite and the filtrate was concentrated under reduced pressure to afford the title compound (15.4 g).

LCMS (method 10-90AB), Retention time=0.65 minutes, [M+H]$^+$=306.1.

A5: (4aR,10aR)-7-methoxy-6-(methoxymethoxy)-1-propyl-1,2,3,4,4a,5,10,10a-octahydrobenzo[g]quinoline To the solution of (4aR,10aR)-6-(methoxymethoxy)-1-propyl-1,2,3,4,4a,5,10,10a-octahydrobenzo[g]quinolin-7-ol (15 g) in MeOH (150 mL) was added drop-wise trimethyl-silyl)diazomethane (TMSCH$_2$N$_2$; 2M in hexane, 246 mL) at 20° C. over 0.5 hours. The mixture was concentrated to afford the title compound (15 g).

A6: (4aR,10aR)-7-methoxy-1-propyl-1,2,3,4,4a,5,10,10a-octahydrobenzo[g]quinolin-6-ol (4aR,10aR)-7-Methoxy-6-(methoxymethoxy)-1-propyl-1,2,3,4,4a,5,10,10a-octahydrobenzo[g]quinoline (15 g) and 4M HCl in MeOH (150 mL) were charged into a reactor (100 mL) at 20° C. The reaction mixture was stirred at 20° C. for 1 hour, before it was concentrated. The residue was dissolved in water (100 mL) and the aqueous layer was basified with solid NaHCO₃ to pH 7-8. The aqueous layer was extracted with EtOAc (100 mL×1, 50 mL×1). The organic layers were combined and washed with brine (100 mL), dried over sodium sulfate, filtered, and concentrated to afford the title compound (7 g).

1H NMR (400 MHz, CDCl3) δ 6.70 (d, J=8.4 Hz, 1H), 6.62 (d, J=8.0 Hz, 1H), 5.71 (br s, 1H), 3.86 (s, 3H), 3.07-3.18 (m, 2H), 3.01 (dd, J=5.2, 17.6 Hz, 1H), 2.72-2.89 (m, 2H), 2.58-2.68 (m, 1H), 2.29-2.44 (m, 2H), 2.24 (dd, J=12.0, 17.6 Hz, 1H), 1.97 (d, J=13.2 Hz, 1H), 1.70-1.92 (m, 3H), 1.54-1.63 (m, 2H), 1.10-1.23 (m, 1H), 0.93 (t, J=7.2 Hz, 3H).

Preparation of Exemplified Compounds of the Invention from Compound (I)

Compound (3): (4aR,10aR)-1-propyl-1,2,3,4,4a,5,10,10a-octahydrobenzo[g]quinoline-6,7-diyl bis(dimethylcarbamate)

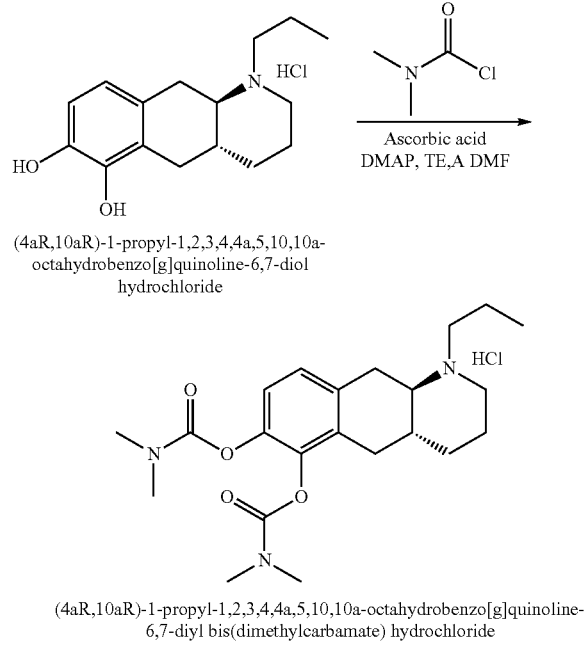

(4aR,10aR)-1-propyl-1,2,3,4,4a,5,10,10a-octahydrobenzo[g]quinoline-6,7-diol hydrochloride (4aR,10aR)-1-propyl-1,2,3,4,4a,5,10,10a-octahydrobenzo[g]quinoline-6,7-diyl bis(dimethylcarbamate) hydrochloride (4aR,10aR)-1-propyl-1,2,3,4,4a,5,10,10a-octahydrobenzo[g]quinoline-6,7-diol hydrochloride (500 mg), ascorbic acid (30 mg) and 4-(dimethylamino)pyridine (11 mg) were weighed into a vial. DMF (5 mL) was added. The vial was evacuated and back-filled with nitrogen. Triethyl amine (0.7 mL) and N,N-dimethylcarbamoylchloride (0.39 mL) were added and the mixture was stirred at room temperature for 2 hours. Then additional triethyl amine (0.7 mL) and N,N-dimethylcarbamoylchloride (0.6 mL) were added and the mixture was stirred at room temperature for 1 hour. The mixture was purified by chromatography (EtOAc/heptane/triethyl amine 20:19:1) to afford a crude product. This material was dissolved in THF (20 mL) and cooled to 0° C. To the thoroughly stirred mixture was dropwise added 0.1 M HCl in THF until slightly acidic. A dense, white precipitate formed gradually. The mixture was stirred on ice. The solid was collected and dried to afford the title compound (233 mg) as a HCl salt.

¹H NMR (600 MHz, DMSO-d6) δ 10.54 (s, 1H), 7.05 (s, 2H), 3.54-3.40 (m, 2H), 3.32-3.26 (m, 1H), 3.26-3.18 (m, 1H), 3.12-2.98 (m, 6H), 2.95 (s, 3H), 2.90 (s, 3H), 2.89 (s, 3H), 2.84 (dd, J=17.3, 4.9 Hz, 1H), 2.25 (dd, J=17.3, 11.8 Hz, 1H), 2.09-2.00 (m, 1H), 2.00-1.88 (m, 2H), 1.88-1.80 (m, 1H), 1.79-1.61 (m, 2H), 1.40-1.28 (m, 1H), 0.96 (t, J=7.4 Hz, 3H).

LCMS (Method 550_ESI): Retention time=0.42 minutes; UV-purity 100%; ELS-purity 100%; m/z=404.5 [M+H]+.

Compound (2): (4aR,10aR)-1-propyl-1,2,3,4,4a,5,10,10a-octahydrobenzo[g]quinoline-6,7-diyl bis(ethylcarbamate)

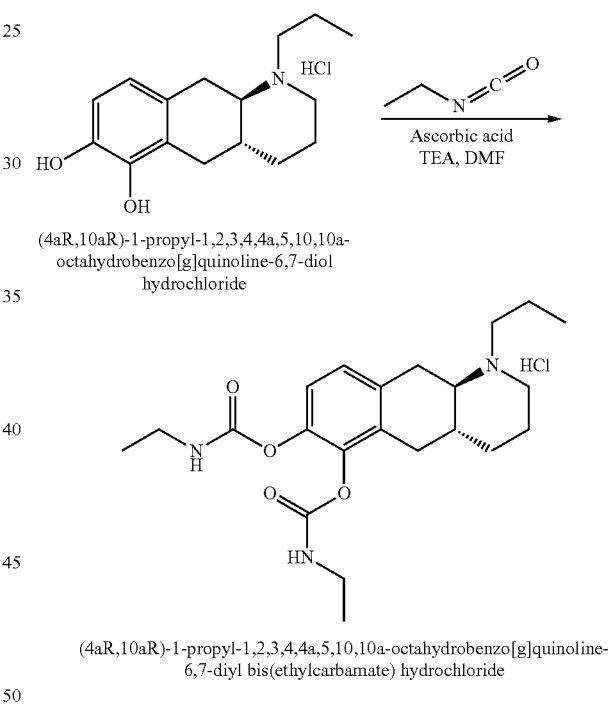

(4aR,10aR)-1-propyl-1,2,3,4,4a,5,10,10a-octahydrobenzo[g]quinoline-6,7-diol hydrochloride (4aR,10aR)-1-propyl-1,2,3,4,4a,5,10,10a-octahydrobenzo[g]quinoline-6,7-diyl bis(ethylcarbamate) hydrochloride (4aR,10aR)-1-propyl-1,2,3,4,4a,5,10,10a-octahydrobenzo[g]quinoline-6,7-diol hydrochloride (500 mg) and ascorbic acid (28 mg) were weighed into a vial, followed by addition of DMF (4.0 mL). The vial was evacuated and back-filled with nitrogen. Triethyl amine (1 mL) and ethyl isocyanate (0.35 mL) were added and the mixture was stirred at room temperature for 2 hours. The mixture was poured into brine and extracted with EtOAc. The organic layer was washed with brine, dried over magnesium sulfate, filtered, and concentrated. The residue was purified by chromatography (EtOAc/heptane/triethylamine 10:9:1) to afford the crude product. This material was dissolved in EtOAc (20 mL) and cooled to 0° C. To the thoroughly stirred mixture was added dropwise 0.2 M HCl in EtOAc until pH 3-4. A white precipitate formed that was collected and dried to afford the title compound (239 mg) as a HCl salt.

¹H NMR (600 MHz, DMSO-d6) δ 10.52 (brs, 1H), 7.78 (t, J=5.6 Hz, 1H), 7.70 (t, J=5.6 Hz, 1H), 7.02 (d, J=8.4 Hz, 1H), 6.98 (d, J=8.4 Hz, 1H), 3.48 (d, J=12.1 Hz, 1H), 3.42 (dd, J=16.0, 5.3 Hz, 1H), 3.35-3.25 (m, 1H), 3.26-3.18 (m, 1H), 3.18-2.95 (m, 7H), 2.78 (dd, J=17.2, 4.9 Hz, 1H), 2.22 (dd, J=17.2, 11.9 Hz, 1H), 2.10-1.89 (m, 3H), 1.87-1.80 (m, 1H), 1.80-1.64 (m, 2H), 1.34 (qd, J=13.1, 4.0 Hz, 1H), 1.14-1.02 (m, 6H), 0.96 (t, J=7.3 Hz, 3H).

LCMS (Method 550): Retention time=0.41 minutes; UV-purity 100%; ELS-purity 98%; m/z=404.6 [M+H]⁺.

Compound (1): (4aR,10aR)-1-propyl-1,2,3,4,4a,5,10,10a-octahydrobenzo[g]quinoline-6,7-diyl bis(m-ethylcarbamate)

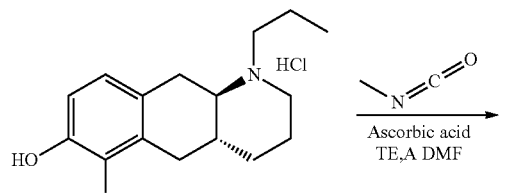

(4aR, 10aR)-1-propyl-1,2,3,4,4a,5,10,10a-octahydrobenzo[g]quinoline-6,7-diol hydrochloride

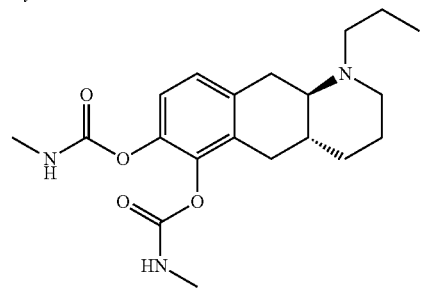

(4aR,10aR)-1-propyl-1,2,3,4,4a,5,10,10a-octahydrobenzo[g]quinoline-6,7-diyl bis(methylcarbamate)

(4aR,10aR)-1-propyl-1,2,3,4,4a,5,10,10a-(4aR,10aR)-1-propyl-1,2,3,4,4a,5,10,10a-octahydrobenzo[g]quinoline-octahydrobenzo[g]quinoline-6,7-diol hydrochloride 6,7-diyl bis(methylcarbamate) (4aR,10aR)-1-propyl-1,2,3,4,4a,5,10,10a-octahydrobenzo[g]quinoline-6,7-diol hydrochloride (500 mg) and ascorbic acid (28 mg) were weighed into a vial, followed by addition of DMF (4.0 mL). The vial was evacuated, and back-filled with nitrogen. Triethyl amine (1.0 mL) and methyl isocyanate (0.21 mL) were added and the mixture was stirred at room temperature for 2 hours. The mixture was poured into brine and extracted with EtOAc. The organic layer was washed with brine, dried over magnesium sulfate, filtered, and concentrated. The residue was purified by chromatography (EtOAc/heptane/triethylamine 14:5:1) to afford a crude product. This material was dissolved in a hot mixture of THF (10 mL) and EtOAc (15 mL). Heptane (10 mL) was added and the mixture was concentrated to a volume of approximately 15 mL. This solution was cooled to 0° C. to precipitate a solid, which was collected and dried to afford the title compound (310 mg).

¹H NMR (600 MHz, DMSO-d6) δ 7.63 (q, J=4.6 Hz, 1H), 7.57 (q, J=4.6 Hz, 1H), 6.97 (d, J=8.3 Hz, 1H), 6.89 (d, J=8.3 Hz, 1H), 3.20 (dd, J=16.3, 4.9 Hz, 1H), 2.91 (d, J=11.2 Hz, 1H), 2.77-2.58 (m, 8H), 2.52-2.43 (m, 1H), 2.31 (ddd, J=13.1, 9.5, 4.8 Hz, 1H), 2.18-2.03 (m, 3H), 1.85-1.77 (m, 1H), 1.65-1.58 (m, 1H), 1.59-1.36 (m, 4H), 1.04 (qd, J=12.8, 4.1 Hz, 1H), 0.86 (t, J=7.3 Hz, 3H).

LCMS (Method 550): Retention time=0.32 minutes; UV-purity 100%; ELS-purity 100%; m/z=376.53 [M+H]+.

Compound (4): ((((4aR,10aR)-7-hydroxy-1-propyl-1,2,3,4,4a,5,10,10a-octahydrobenzo[g]-quinolin-6-yl)oxy)carbonyl)glycine Compound (4) can for example be prepared from the intermediate (4aR,10aR)-7-(benzyloxy)-1-propyl-2H,3H,4H,4aH,5H,10H,10aH-benzo[g]quinolin-6-ol hydrogen iodide (compound A2-HI) using a two-step process as described below:

Preparation of benzyl ((((4aR,10aR)-7-(benzyloxy)-1-propyl-1,2,3,4,4a,5,10,10a-octahydrobenzo[g]quinolin-6-yl)oxy)carbonyl)glycinate (Compound A7)

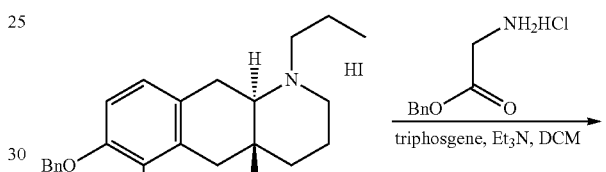

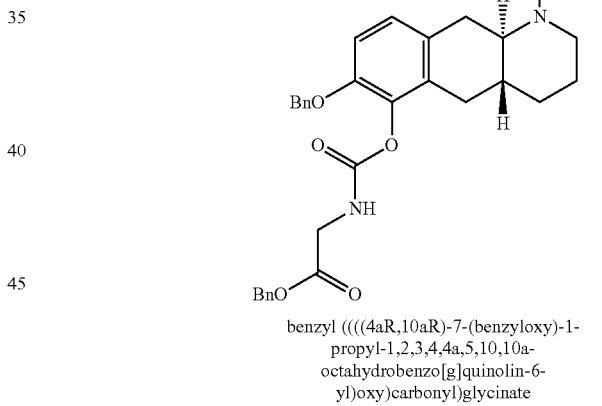

benzyl ((((4aR,10aR)-7-(benzyloxy)-1-propyl-1,2,3,4,4a,5,10,10a-octahydrobenzo[g]quinolin-6-yl)oxy)carbonyl)glycinate To a stirred solution of benzyl 2-aminoacetate hydrochloride (1.01 g, 5.0 mmol) and triphosgene (0.59 g, 2.0 mmol) in DCM (50 mL) was added Et₃N (1.69 g, 16.7 mmol) at 0° C. The resulting mixture was stirred for 1 hour at 0° C. To the above mixture was added (4aR,10aR)-7-(benzyloxy)-1-propyl-2H,3H,4H,4aH,5H,10H,10aH-benzo[g]quinolin-6-ol hydrogen iodide (2.00 g, 4.2 mmol). The resulting mixture was stirred overnight at room temperature. The reaction was quenched with water/ice (50 mL). The aqueous layer was extracted with DCM (3×50 mL). The combined organic extracts were concentrated. The residue was purified by reverse flash chromatography with the following conditions: column, C18 silica gel; mobile phase, MeCN in water (0.05% TFA), 0% to 75% gradient in 30 minutes; detector, UV 220 nm to afford the title compound (2.1 g) sufficiently pure for the next step.

Preparation of ((((4aR,10aR)-7-hydroxy-1-propyl-1,2,3,4,4a,5,10,10a-octahydrobenzo[g]quinolin-6-yl)oxy)carbonyl)glycine (Compound (4)) from compound (A7)

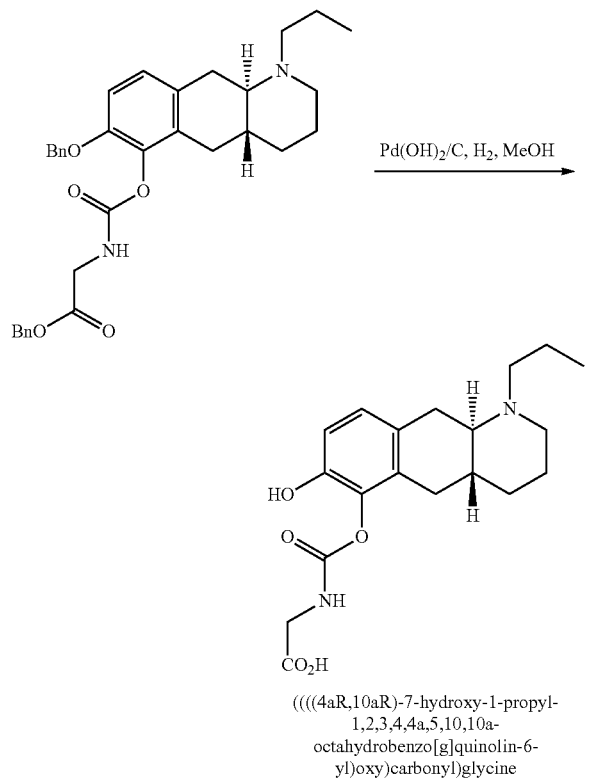

((((4aR,10aR)-7-hydroxy-1-propyl-1,2,3,4,4a,5,10,10a-octahydrobenzo[g]quinolin-6-yl)oxy)carbonyl)glycine To a solution of benzyl ((((4aR,10aR)-7-(benzyloxy)-1-propyl-1,2,3,4,4a,5,10,10a-octahydrobenzo[g]quinolin-6-yl)oxy)carbonyl)glycinate (2.10 g, 3.9 mmol) in MeOH (100 mL) was added Pd(OH)$_2$/C (10%, 0.4 g) under nitrogen atmosphere in a 250 mL round-bottom flask. The mixture was hydrogenated at room temperature for 2 hours under hydrogen atmosphere using a hydrogen balloon, filtered through a Celite pad, and concentrated under reduced pressure. The residue was purified by trituration with EtOH (100 mL) to afford the title compound (693 mg).

LC/MS: Retention time: 1.35 minutes, UV-purity: 95.5%; (ES, m/z): [M+H]+ 363. Instrument: Shimadzu LCMS-2020 fitted with a Shim-Pack XR-ODS C18, L=50 mm, D=3.0 mm column operated at 40° C. Mobile phase A: 0.05% TFA in water; mobile phase B: 0.05% TFA in acetonitrile. Flow rate 1.2 mL/min.

Gradient:

0-3.2 minutes A:B 95:5;

3.2 min-3.7 min: A:B 1:1;

3.7 min-4.75 min: A:B 0:1;

4.75 min-5.0 min: A:B 95:5.

1H NMR (400 MHz, DMSO) δ 6.84-6.82 (d, 1H), 6.73-6.71 (d, 1H), 3.73-3.69 (m, 3H), 3.52-3.49 (d, 1H), 3.30-3.27 (m, 2H), 2.85-2.79 (m, 2H), 2.72-2.66 (m, 2H), 2.32-2.22 (m, 1H), 1.94-1.57 (m, 6H), 1.32-1.27 (m, 1H), 0.98-0.91 (t, 3H).

Compound (5): ((((4aR,10aR)-6-hydroxy-1-propyl-1,2,3,4,4a,5,10,10a-octahydrobenzo[g]-quinolin-7-yl)oxy)carbonyl)glycine Compound (5) can for example be prepared from the intermediate (4aR,10aR)-7-(benzyloxy)-1-propyl-2H,3H,4H,4aH,5H,10H,10aH-benzo[g]quinolin-6-ol hydrogen iodide compound (A2-HI) using a four-step process as described below:

Preparation of (4aR,10aR)-7-(benzyloxy)-6-(methoxymethoxy)-1-propyl-1,2,3,4,4a,5,10,10a-octahydrobenzo[g]quinoline (Compound (A3)

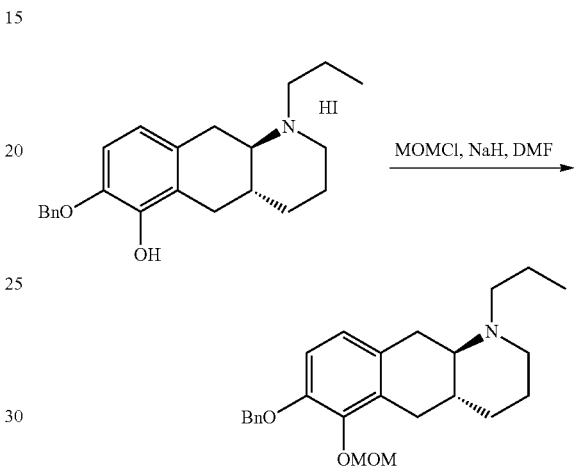

(4aR,10aR)-7-(benzyloxy)-6-(methoxymethoxy)-1-propyl-1,2,3,4,4a,5,10,10a-octahydrobenzo[g]quinoline To a stirred solution of (4aR,10aR)-7-(benzyloxy)-1-propyl-2H,3H,4H,4aH,5H,10H,10aH-benzo[g]quinolin-6-ol hydrogen iodide (5.00 g, 10.4 mmol) in DMF (100 mL) was added NaH (60% oil dispersion; 1.04 g, 26.0 mmol) portion-wise at 0° C. The resulting mixture was stirred for 0.5 hours at 0° C. under nitrogen atmosphere. To the above mixture was added MOM-Cl (0.83 g, 12.4 mmol) drop-wise at 0° C. The resulting mixture was stirred for 2 hours at 0° C. before the reaction was quenched with water (300 mL). The resulting mixture was extracted with EtOAc (3×200 mL), and the combined organic extracts were concentrated. The residue was purified by reverse flash chromatography with the following conditions: column, C18 silica gel; mobile phase, MeCN in water (10 mM NH$_4$HCO$_3$), 0% to 80% gradient in 40 minutes; detector, UV 220 nm to afford the title compound (2.4 g) sufficiently pure for the next step.

Preparation of (4aR,10aR)-6-(methoxymethoxy)-1-propyl-1,2,3,4,4a,5,10,10a-octahydrobenzo[g]quinolin-7-ol (Compound (A4))

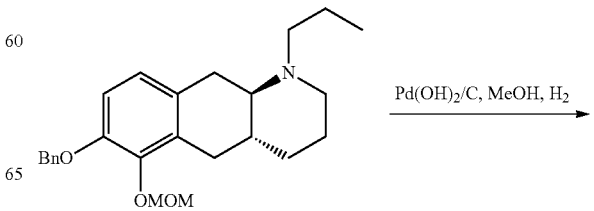

-continued

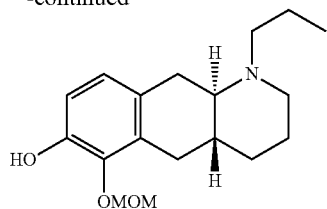

(4aR,10aR)-6-(methoxymethoxy)-1-propyl-1,2,3,4,4a,5,10,10a-octahydrobenzo[g]quinolin-7-ol To a solution of (4aR,10aR)-7-(benzyloxy)-6-(methoxymethoxy)-1-propyl-2H,3H,4H,4aH,5H,10H,10aH-benzo [g]quinoline (2.40 g, 6.1 mmol) in MeOH (50 mL) was added Pd(OH)$_2$/C (0.5 g, 10%) under nitrogen atmosphere. The mixture was hydrogenated at room temperature overnight under hydrogen atmosphere using a hydrogen balloon. The crude mixture was filtered through a Celite pad and concentrated under reduced pressure to afford the title compound (1.9 g) sufficiently pure for the next step.

Preparation of tert-butyl ((((4aR,10aR)-1-ethyl-6-(methoxymethoxy)-1,2,3,4,4a,5,10,10a-octahydrobenzo[g]quinolin-7-yl)oxy)carbonyl)glycinate (Compound (A8))

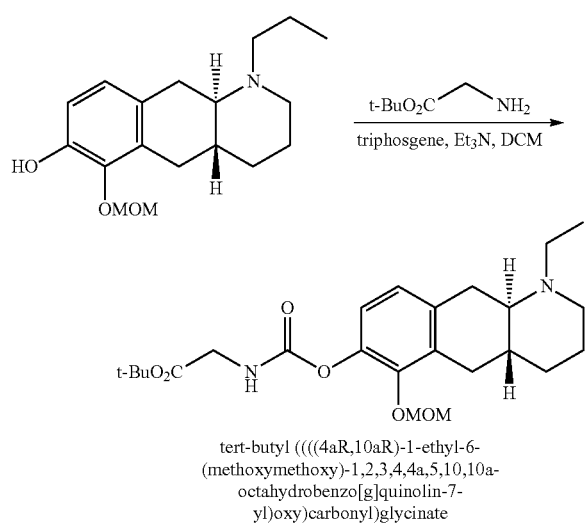

tert-butyl ((((4aR,10aR)-1-ethyl-6-(methoxymethoxy)-1,2,3,4,4a,5,10,10a-octahydrobenzo[g]quinolin-7-yl)oxy)carbonyl)glycinate To a stirred solution of tert-butyl 2-aminoacetate (0.52 g, 3.9 mmol) and triphosgene (0.47 g, 1.6 mmol) in DCM (30 mL) was added Et$_3$N (1.33 g, 13.1 mmol) at 0° C. The resulting mixture was stirred for 1 hour at 0° C. before addition of (4aR,10aR)-6-(methoxymethoxy)-1-propyl-2H,3H,4H,4aH,5H,10H,10aH-benzo[g]quinolin-7-ol (1.00 g, 3.3 mmol). The resulting mixture was stirred overnight at room temperature, before the reaction was quenched with water/ice (50 mL). The aqueous layer was extracted with DCM (3×50 mL), and the combined organic extracts were concentrated. The residue was purified by reverse flash chromatography with the following conditions: column, C18 silica gel; mobile phase, MeCN in water (0.05% TFA), 0% to 75% gradient in 30 min; detector, UV 220 nm to afford the title compound (0.8 g) sufficiently pure for the next step.

Preparation of ((((4aR,10aR)-6-hydroxy-1-propyl-1,2,3,4,4a,5,10,10a-octahydrobenzo[g]quinolin-7-yl)oxy)carbonyl)glycine (Compound (5)) from Compound (A8)

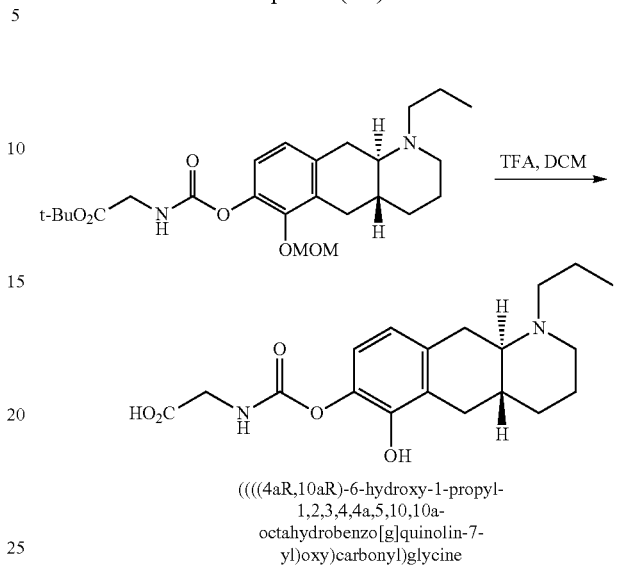

((((4aR,10aR)-6-hydroxy-1-propyl-1,2,3,4,4a,5,10,10a-octahydrobenzo[g]quinolin-7-yl)oxy)carbonyl)glycine To a stirred solution of tert-butyl ((((4aR,10aR)-1-ethyl-6-(methoxymethoxy)-1,2,3,4,4a,5,10,10a-octahydrobenzo [g]quinolin-7-yl)oxy)carbonyl)glycinate (0.8 g, 1.7 mmol) in DCM (10 mL) was added TFA (3.0 mL). The resulting mixture was stirred for 4 hours at room temperature, before it was concentrated. The residue was purified by Prep-HPLC with the following conditions (Column: XBridge Shield RP18 OBD Column, 19*250 mm, 10 um; Mobile Phase A: Water (0.05% TFA), Mobile Phase B: ACN; Flow rate:25 mL/min; Gradient: 12% B to 14% B in 10 minutes; 254 nm to afford the title compound (225 mg).

LC/MS: Retention time: 1.48 min, UV-purity: 97.3%; (es, m/z): [M+H]$^+$ 363. Instrument: Shimadzu LCMS-2020 fitted with a Shim-Pack XR-ODS C18, L=50 mm, D=3.0 mm column operated at 40° C. Mobile phase A: 0.05% TFA in water; mobile phase B: 0.05% TFA in acetonitrile. Flow rate 1.2 mL/min. Gradient:

0-3.2 min A:B 95:5;

3.2 min-3.7 min: A:B 1:1;

3.7 min-4.75 min: A:B 0:1;

4.75 min-5.0 min: A:B 95:5.

$^1$H NMR (400 MHz, DMSO) δ 6.84-6.82 (d, 1H), 6.73-6.71 (d, 1H), 3.79 (s, 2H), 3.64-3.52 (d, 1H), 3.29-3.28 (m, 1H), 3.14-2.92 (m, 4H), 2.80-2.72 (m, 2H), 2.22-2.18 (m, 1H), 1.94-1.57 (m, 6H), 1.40-1.31 (m, 1H), 0.98-0.94 (t, 3H).

Compound (6): (S)-2-amino-3-(3-(((((4aR,10aR)-7-hydroxy-1-propyl-1,2,3,4,4a,5,10,10a-octahydrobenzo[g]quinolin-6-yl)oxy)carbonyl)amino)phenyl)propanoic Acid Compound (6) can for example be prepared using a five step process as described below from the intermediate (2S)-2-[(tert-butoxycarbonyl)amino]-3-(3-nitrophenyl)propanoic acid compound (A9) (commercially available e.g. from Nan Jing Peptide Biotechnology Co. Ltd)

Preparation of benzyl (S)-2-((tert-butoxycarbonyl)amino)-3-(3-nitrophenyl)propanoate (Compound (A10)) from compound (A9)

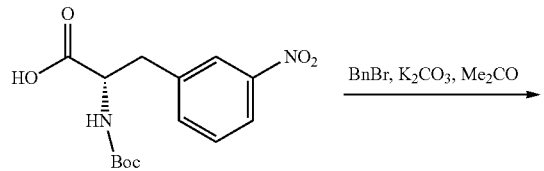

benzyl (S)-2-((tert-butoxycarbonyl)amino)-3-(3-nitrophenyl)propanoate

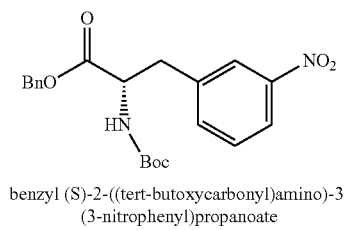

To a stirred solution of (2S)-2-[(tert-butoxycarbonyl)amino]-3-(3-nitrophenyl)propanoic acid (5.00 g, 16.1 mmol) and BnBr (3.31 g, 19.3 mmol) in acetone (100 mL) was added $K_2CO_3$ (4.45 g, 32.2 mmol). The resulting mixture was stirred overnight at 50° C. The resulting mixture was filtered, and the filtrate was concentrated. The residue was purified by silica gel column chromatography (eluent pentane/EtOAc 10:1) to afford the title compound (4.0 g) sufficiently pure for the next step.

Preparation of benzyl (S)-3-(3-aminophenyl)-2-((tert-butoxycarbonyl)amino)propanoate (Compound (A11)) from Compound (A10)

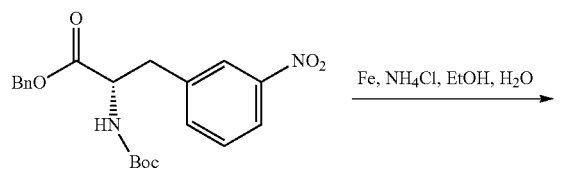

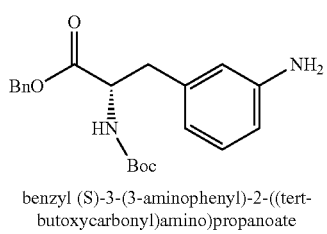

benzyl (S)-3-(3-aminophenyl)-2-((tert-butoxycarbonyl)amino)propanoate

To a stirred solution of benzyl (2S)-2-[(tert-butoxycarbonyl)amino]-3-(3-nitrophenyl)propanoate (4.0 g, 9.9 mmol) and $NH_4Cl$ (2.14 g, 40 mmol) in EtOH (100 mL) and $H_2O$ (25 mL) was added Fe (1.67 g, 30 mmol). The resulting mixture was stirred for 3 hours at 80° C. The resulting mixture was diluted with water (200 mL) and approximately 100 mL of the solvent was removed under vacuum. The resulting mixture was extracted with EtOAc (2×100 mL), and the combined organic extracts were concentrated. The residue was purified by silica gel column chromatography (eluent: pentane/EtOAc 5:1) to afford the title compound (3.1 g) sufficiently pure for the next step.

Preparation of benzyl (S)-3-(3-(((((4aR,10aR)-7-(benzyloxy)-1-propyl-1,2,3,4,4a,5,10,10a-octahydrobenzo[g]-quinolin-6-yl)oxy)carbonyl)amino)phenyl)-2-((tert-butoxycarbonyl)amino)propanoate (Compound (A12)) from Compound (A11)

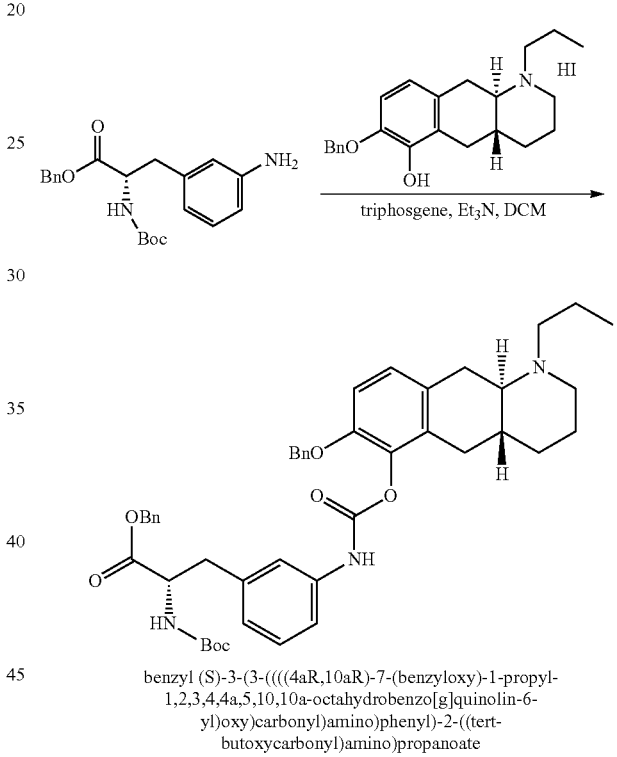

benzyl (S)-3-(3-(((((4aR,10aR)-7-(benzyloxy)-1-propyl-1,2,3,4,4a,5,10,10a-octahydrobenzo[g]quinolin-6-yl)oxy)carbonyl)amino)phenyl)-2-((tert-butoxycarbonyl)amino)propanoate To a stirred solution of benzyl (2S)-3-(3-aminophenyl)-2-[(tert-butoxycarbonyl)amino]propanoate (928 mg, 2.5 mmol) and triphosgene (297 mg, 1.0 mmol) in DCM (30 mL) was added $Et_3N$ (845 mg, 8.4 mmol) at 0° C. The resulting mixture was stirred for 1 hour at 0° C. before addition of (4aR,10aR)-7-(benzyloxy)-1-propyl-2H,3H,4H,4aH,5H,10H,10aH-benzo[g]quinolin-6-ol hydrogen iodide (1.00 g, 2.1 mmol). The resulting mixture was stirred overnight at room temperature. The reaction was quenched with water/ice (50 mL). The aqueous layer was extracted with DCM (3×50 mL). The combined organic extracts were concentrated. The residue was purified by reverse flash chromatography with the following conditions: column, C18 silica gel; mobile phase, MeCN in water (0.05% TFA), 0% to 65% gradient in 40 minutes; detector, UV 220 nm to afford the title compound (730 mg) sufficiently pure for the next step.

Preparation of benzyl (S)-2-amino-3-(3-(((((4aR, 10aR)-7-(benzyloxy)-1-propyl-1,2,3,4,4a,5,10,10a-octahydrobenzo[g]quinolin-6-yl)oxy)carbonyl) amino)phenyl)propanoate trifluoroacetate (Compound (A13)) from Compound (A12)

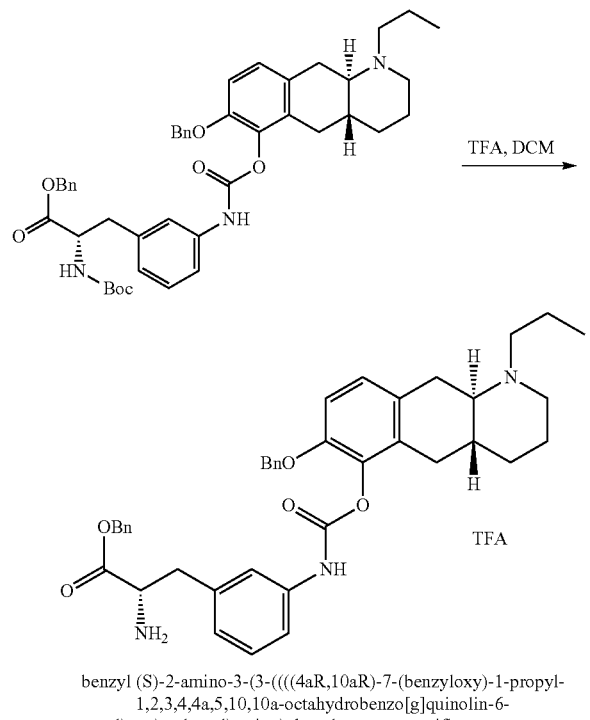

benzyl (S)-2-amino-3-(3-((((4aR,10aR)-7-(benzyloxy)-1-propyl-1,2,3,4,4a,5,10,10a-octahydrobenzo[g]quinolin-6-yl)oxy)carbonyl)amino)phenylpropanoate trifluoroacetate To a stirred solution benzyl 3-[3-[([[(4aR,10aR)-7-(benzyloxy)-1-propyl-2H,3H,4H,4aH,5H,10H,10aH-benzo[g]quinolin-6-yl]oxy]carbonyl)amino]phenyl]-2-[(tert-butoxycarbonyl)amino]propanoate (730 mg, 1.0 mmol) in DCM (15 mL) was added TFA (3.0 mL). The resulting mixture was stirred for 6 hours at room temperature before it was concentrated to afford the title compound (810 mg) sufficiently pure for the next step.

Preparation of (S)-2-amino-3-(3-(((((4aR,10aR)-7-hydroxy-1-propyl-1,2,3,4,4a,5,10,10a-octahydrobenzo[g]quinolin-6-yl)oxy)carbonyl)amino)phenyl)propanoic Acid (Compound (6)) from Compound (A13)

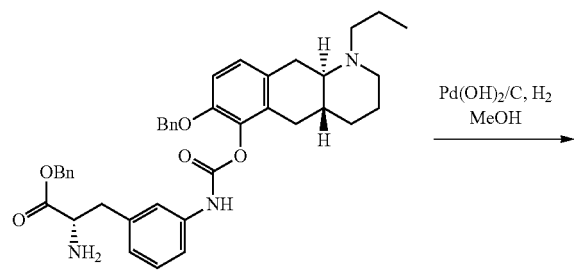

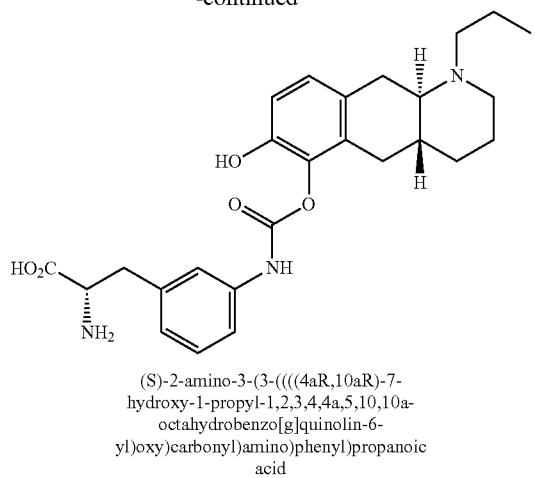

(S)-2-amino-3-(3-((((4aR,10aR)-7-hydroxy-1-propyl-1,2,3,4,4a,5,10,10a-octahydrobenzo[g]quinolin-6-yl)oxy)carbonyl)amino)phenyl)propanoic acid To a solution of benzyl 3-[3-[([[(4aR,10aR)-7-(benzyloxy)-1-propyl-2H,3H,4H,4aH,5H,10H,10aH-benzo[g]quinolin-6-yl]oxy]carbonyl)amino]phenyl]-2-aminopropanoate trifluoroacetate (810 mg, 1.3 mmol) in MeOH (100 mL) was added Pd(OH)$_2$/C (0.2 g, 10%) under nitrogen atmosphere in a 250 mL round-bottom flask. The mixture was hydrogenated at room temperature for 2 hours using a hydrogen balloon, filtered through a Celite pad, and concentrated. The residue was purified by Prep-HPLC with the following conditions (Column: XBridge Shield RP18 OBD Column, 19*250 mm, 10 um; Mobile Phase A: Water (0.05% TFA), Mobile Phase B: ACN; Flow rate:25 mL/min; Gradient: 10% B to 12% B in 10 minutes; 254 nm to afford the title compound (380 mg).

LC/MS: Retention time: 1.71 min; UV-purity: 96.1; (ES, m/z): [M+H]$^+$ 468. Instrument: Shimadzu LCMS-2020 fitted with a Shim-Pack XR-ODS C18, L=50 mm, D=3.0 mm column operated at 40° C. Mobile phase A: 0.05% TFA in water; mobile phase B: 0.05% TFA in acetonitrile. Flow rate 1.2 mL/min. Gradient: 0-3.2 min A:B 95:5; 3.2 min-3.7 min: A:B 1:1; 3.7 min-4.75 min: A:B 0:1; 4.75 min-5.0 min: A:B 95:5.

$^1$H NMR (400 MHz, DMSO) δ 7.73-7.41 (d, 2H), 7.30-7.26 (t, 1H), 6.95-6.93 (d, 1H), 6.90-6.88 (d, 1H), 6.80-6.78 (d, 1H), 4.14-4.11 (t, 1H), 3.54-3.51 (d, 1H), 3.28-3.0 (m, 5H), 2.87-2.78 (m, 3H), 2.32-2.28 (m, 1H), 1.91-1.66 (m, 6H), 1.40-1.30 (m, 1H), 0.98-0.95 (t, 3H).

In Vitro and In Vivo Characterization of Compounds of the Invention

Example 1: Conversion of Compounds of the Invention in Human Plasma

Frozen human plasma was thawed and then centrifuged at 3200×g for 5 minutes to remove debris. The pH value of the supernatant was then measured and adjusted to 7.4±0.1 by adding 1% phosphoric acid or 1 N sodium hydroxide. 2 μL of dosing solution (50 μM for test compounds and 100 μM for positive control (propantheline bromide)) was mixed with 98 μL of blank plasma to achieve 1 μM test compound and 2 μM positive control of final concentration. The mixture was incubated, and samples were withdrawn from the incubations at the pre-determined time points of 0, 0.5, 1, 2, 4 and 6 hours (in duplicate) at 37° C. in water bath. At each corresponding time point 10 μL inhibitor and 20 μL ascorbic acid and 2 μL formic acid (20%) are added, and then added 400 µL of "stop solution" (200 ng/mL tolbutamide plus 200 ng/mL labetalol in 50% ACN/MeOH) to precipitate protein. The substance was mixed thoroughly and thereafter Centrifugated at 4,000 rpm for 20 minutes. Then an aliquot of supernatant (50 µL) was transferred from each well to a sample plate and mixed with 100 µL ultrapure water. The plate was shaked at 800 rpm for about 10 minutes before submitting to LC-MS/MS analysis.

Instrumentation Used for Analysis of Plasma Incubation Samples:

Mass spectrometer (LC-MS/MS) Shimadzu LC 20-AD Shimadzu UHPLC API 4000. Analytical column ACQUITY UPLC® BEH Phenyl 1.7 µm 2.1×50 mm. Mobile phase A: 0.1% Formic Acid in Water. Mobile phase B: 0.1% Formic Acid in Acetonitrile. Gradient run from 95/5% to 5/95 in 2.0 minutes. Flow rate 0.7 mL/min. MRM monitoring (multiple reaction monitoring) of test item and the added analytical standards (Labetalol or Tolbutamide).

Example 2: 5-HT2B Agonist Activity and Binding Assay

5-HT2B Agonist Activity Assay

Evaluation of the agonist activity of compounds (I), (Ia) and (Ib) at the human 5-HT2B receptor was performed by Eurofins/Cerep (France) measuring the compound effects on inositol monophosphate (IP1) production using the HTRF detection method. Briefly, the human 5-HT2B receptor was expressed in transfected CHO cells. The cells were suspended in a buffer containing 10 mM Hepes/NaOH (pH 7.4), 4.2 mM KCl, 146 mM NaCl, 1 mM CaCl$_2$, 0.5 mM MgCl2, 5.5 mM glucose and 50 mM LiCl, then distributed in microplates at a density of 4100 cells/well and incubated for 30 min at 37° C. in the presence of buffer (basal control), test compound or reference agonist. For stimulated control measurement, separate assay wells contained 1 µM 5-HT. Following incubation, the cells were lysed and the fluorescence acceptor (fluorophen D2-labeled IP1) and fluorescence donor (anti-IP1 antibody labeled with europium cryptate) were added. After 60 minutes at room temperature, the fluorescence transfer was measured at lambda(Ex) 337 nm and lambda (Em) 620 and 665 nm using a microplate reader (Rubystar, BMG). The IP1 concentration was determined by dividing the signal measured at 665 nm by that measured at 620 nm (ratio). The results were expressed as a percent of the control response to 1 µM 5-HT. The standard reference agonist was 5-HT, which was tested in each experiment at several concentrations to generate a concentration-response curve from which its $EC_{50}$ value is calculated as described above for dopamine functional assays.

5-HT2B Binding Assay

Evaluation of the affinity of compounds for the human 5-HT2B receptor was determined in a radioligand binding assay at Eurofins/Cerep (France). Membrane homogenates prepared from CHO cells expressing the human 5HT2B receptor were incubated for 60 minutes at room temperature with 0.2 nM [125I](±)DOI (1-(4-iodo-2, 5-dimethoxyphenyl)propan-2-amine) in the absence or presence of the test compound in a buffer containing 50 mM Tris-HCl (pH 7.4), 5 mM MgCl$_2$, 10 µM pargyline and 0.1% ascorbic acid. Nonspecific binding is determined in the presence of 1 µM (±)DOI. Following incubation, the samples were filtered rapidly under vacuum through glass fiber filters (GF/B, Packard) presoaked with 0.3% polyethyleneimine (PEI) and rinsed several times with ice-cold 50 mM Tris-HCl using a 96-sample cell harvester (Unifilter, Packard). The filters were dried and counted for radioactivity in a scintillation counter (Topcount, Packard) using a scintillation cocktail (Microscint 0, Packard). The results are expressed as a percent inhibition of the control radioligand specific binding. The standard reference compound was (±)DOI, which was tested in each experiment at several concentrations to obtain a competition curve from which its $IC_{50}$ is calculated.

TABLE 3

In vitro activities for the compounds (1)-(3) of the invention obtained according to Example 2

| | Compound | 5-HT2B EC50 (nM)/Emax |
|---|---|---|
| Parent compound | (I) | 2900 nM/50% |
| Prodrugs in the state of the art | (Ia) | >6000 nM, 58% @30 µM |
| | (Ib) | 3.8 nM/79% |
| | (Ic) | −5% @10 µM |
| Compounds of the invention | Compound (1) | 3% @10 µM |
| | Compound (2) | 3% @10 µM |
| | Compound (3) | 4% @10 µM |

* indicate binding affinity (% inhibition of control, specific binding at concentration indicated)

Example 3: PK Experiments in Rats

For all the experiments, blood samples of approximately 0.68 mL were drawn from the tail or sublingual vein and put into K$_3$EDTA tubes that had been pre-cooled and prepared with stabilizing solution consisting of 80 µL ascorbic acid and 40 µL 100 mM D-saccharic acid 1,4 lactone in water. The tubes were inverted gently 6-8 times to ensure thorough mixing and then placed in wet ice. The collecting tube was placed in wet ice for up to 30 minutes until centrifugation. Once removed from the wet ice the centrifugation was initiated immediately. Immediately after end of centrifugation the samples were returned to wet ice. Three sub-samples of 130 µL plasma were transferred to each of three appropriately labelled cryo tubes containing 6.5 µL pre-cooled formic acid (20%) (the tubes were pre-spiked and stored refrigerated prior to use). The tube lid was immediately replaced, and the plasma solution was thoroughly mixed by inverting gently 6-8 times. The samples were stored frozen at nominally −70° C. within 60 minutes after sampling. Centrifugation conditions at 3000 G for 10 minutes at 4° C. Plasma was placed on water-ice following collection. Final storage at approximately −70° C.

Plasma samples were analyzed by solid phase extraction or direct protein precipitation followed by UPLC-MS/MS. MS detection using electrospray in the positive ion mode with monitoring of specific mass-to-charge transitions for compound (I) using internal standards for correcting the response. The concentration-time data was analyzed, using standard software using appropriate noncompartmental techniques to obtain estimates of the derived PK parameters.

Instrumentation Used for Analysis of Compound (I) from Dosing Compound (Ia):

Mass spectrometer (LC-MS/MS) Waters Acquity-Sciex API 5000. Analytical column Waters BEH UPLC Phenyl 100×2.1 mm column, 1.7 µm particle size. Mobile phase A: 20 mM ammonium formate (aq)+0.5% formic acid. Mobile phase B: Acetonitrile. Gradient run from 95/5% to 2/98 in 6.1 minutes. Flow rate 0.5 mL/min. MRM monitoring (multiple reaction monitoring) of test item and the added analytical standards Dosing and Blood Sampling:

Han Wistar rats were supplied by Charles River Laboratories, Sulzfeld, Germany. An artificial, automatically controlled, light and dark cycle of 12 hours was maintained. The rats received a standard laboratory diet from Brogaarden (Altromin 1324 pellets). The rats had unrestricted access to the diet. During the study (a 4-week toxicity study) the rats received once daily doses of (Ia) orally by gavage. From rats given 300 µg/kg (Ia), blood samples) from 3 male satellite animals were collected on the following time points at Day 29: 0.5, 1, 2, 4, 6, 8, 12 and 24 hours after dosing.

Instrumentation Used for Analysis of Compound (I) from Dosing of Compound (Ib):

Mass spectrometer (LC-MS/MS) Waters Acquity-Sciex API 5000. Analytical column Waters BEH UPLC Phenyl 100×2.1 mm column, 1.7 µm particle size. Mobile phase A: 20 mM ammonium formate (aq)+0.5% formic acid. Mobile phase B: Acetonitrile. Gradient run from 95/5% to 2/98 in 6.1 minutes. Flow rate 0.5 mL/min. MRM monitoring of test item and the added analytical standards.

Dosing and Blood Sampling:

Han Wistar rats were supplied by Charles River Laboratories, UK. An artificial, automatically controlled, light and dark cycle of 12 hours was maintained. The rats received a standard laboratory diet (Teklad 2014C Diet.). The rats had unrestricted access to the diet. During the study (a 26-week toxicity study) the rats received once daily doses of (Ib) orally by gavage. From rats given 300 µg/kg (Ib), blood samples from 3 male satellite animals were collected on the following time points at day 182: 0.5, 1, 2, 4, 8 and 24 hours after dosing.

Instrumentation Used for Analysis of Compound (I) from Dosing of Compounds (Ic), Compound (1), Compound (2) and Compound (3)

Mass spectrometer (LC-MS/MS) Waters Acquity—Waters Xevo TQ-S. Analytical column Acquity BEH C18 100×2.1 mm, 1.7 µm. Mobile phase A: 20 mM NH$_4$—Formate+0.2% formic acid. Mobile phase B: Acetonitrile+0.2% formic acid. Gradient run from 95/5% to 5/95% in 11.0 minutes. Flow rate 0.3 mL/min. MRM monitoring of test item and the added analytical standards.

Dosing and Blood Sampling:

Han Wistar rats were supplied by Envigo, UK. An artificial, automatically controlled, light and dark cycle of 12 hours was maintained. The rats received a standard laboratory diet Teklad 2014C. The rats had unrestricted access to the diet. Male Han Wistar rats were dosed a single oral gavage administration of test compound orally by gavage. Rats were given 494 µg/kg (Ic), 0.505 mg/kg compound (I), 0.505 mg/kg compound (2) and 0.430 mg/kg compound (3). Blood samples from 3 male animals were collected on the following time points at Day 1: 1, 2, 4, 6, 8, and 24 hours after dosing Example 4: Competitive Binding Studies The following assay as described in WO06014429 is used for determining the binding affinity for hPEPT1 of amino acid or peptide carbamate derivatives of the invention:

Ki values for the amino acid or peptide-carbamate derivative compounds (1)-(6) can be determined in the hPEPT1 over-expressing cell line (DC5) using 3H glycine-sarcosine (Gly-Sar). DC5 cells are plated (12,000 cells/well) in 96-well tissue culture plates (Falcon) and allowed to grow for 4 days. The cells are washed once with 200 micro L of uptake buffer and aspirated. The plates are cooled to 4° C. and 25 micro L of uptake buffer containing 50 micro M Gly-Sar (0.5 micro Ci/ml) are added. The uptake buffer also contains the test compounds over a range of concentrations. Uptake is initiated by placing the plate in a shaker water bath (37° C.) and is terminated at 10 minutes by rapid washing with multiple changes of 4° C. PBS (Sigma). The radioactive peptide is extracted from the cell layer with 200 micro L of methanol: water (1:1) and counted in 4 mL of CytoScint ESTM scintillation cocktail (ICN). Non-linear regression analysis of the data is used to determine the IC50 using the solver function in Microsoft Excel.

The invention claimed is:

1. A compound according to formula (Ie)

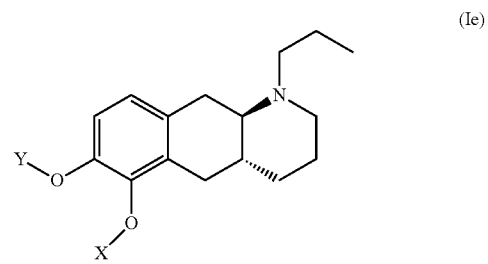

(Ie)

wherein Y is selected from H and a carbamoyl group of the formula (CONR1R2) with the formula below

TABLE 4

PK parameters for (4aR,10aR)-1-Propyl-1,2,3,4,4a,5,10,10a-octahydro-benzo[g]quinoline-6,7-diol (compound (I)) after oral dosing of 0.300 mg/kg (Ia), 0.300 mg/kg (Ib), 494 u.g/kg (Ic), 0.505 mg/kg compound (1), 0.505 mg/kg compound (2) and 0.430mg/kg compound (3) to Wistar rats according to Example 3.

| | compound | $T_{max}$ (h) | $C_{max}$ (pg/mL) | $AUC_{0-24}$ (pg*h/mL) | Exposure at 24 h (pg/mL) |
|---|---|---|---|---|---|
| Prodrugs in the state of the art | (Ia) | 1.0 | 3160 | 13600 | 48 ± 26 |
| | (Ib) | 1.0 | 4990 | 31000 | 147 ± 28 |
| | (Ic) | 1.0 | 14 | 104 | |
| Examples of compounds of the invention | Compound (1) | 4 | 63.5 | 1310 | 47 ± 14 |
| | Compound (2) | 8 | 82.5 | 1740 | 67 ± 10 |
| | Compound (3) | 24 | 93.5 | 1920 | 94 ± 8 |

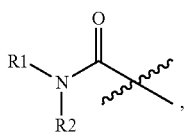

(CONR1R2)

and wherein X is selected from H and a carbamoyl group of the formula (CONR3R4) with the formula below

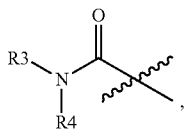

(CONR3R4)

and
wherein Y and X are not both H, and
wherein R1, R2, R3 and R4 are each individually selected from the group consisting of H, $C_{1-6}$ alkyl, an amino acid, an amino acid residue and a peptide;
or a pharmaceutically acceptable salt thereof.

2. The compound according to claim 1, wherein at least one of R1, R2, R3 and R4 is an amino acid, an amino acid residue or a peptide.

3. The compound according to claim 1, wherein at least one of R1, R2, R3 and R4 is an amino acid or an amino acid residue selected from the group consisting of arginine, lysine, aspartic acid, glutamic acid, glutamine, asparagine, histidine, serine, threonine, tyrosine, cysteine, tryptophan, methionine, alanine, isoleucine, leucine, phenylalanine, valine, proline and glycine.

4. The compound according to claim 1, wherein at least one of R1, R2, R3 and R4 is a peptide comprising two or more amino acid residues selected from the group consisting of arginine, lysine, aspartic acid, glutamic acid, glutamine, asparagine, histidine, serine, threonine, tyrosine, cysteine, tryptophan, methionine, alanine, isoleucine, leucine, phenylalanine, valine, proline and glycine residues.

5. The compound according to claim 1 said compound having the formula (Id)

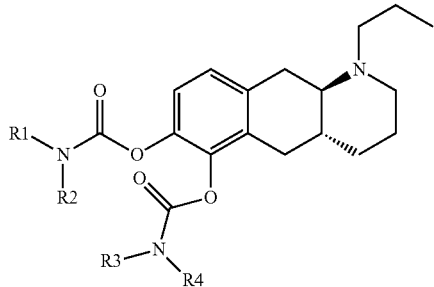

(Id)

wherein R1, R2, R3 and R4 are each individually selected from the group consisting of H and $C_{1-6}$ alkyl;
or a pharmaceutically acceptable salt thereof.

6. The compound or pharmaceutically acceptable salt according to claim 5, wherein
R1=R3 and R2=R4.

7. The compound or pharmaceutically acceptable salt according to claim 5, wherein R1 and R3 are the same $C_{1-6}$ alkyl; and
R2 and R4 are the same $C_{1-6}$ alkyl.

8. The compound according to claim 1, wherein the compound is selected from the group consisting of:
  (4aR,10aR)-1-propyl-1,2,3,4,4a,5,10,10a-octahydrobenzo[g]quinoline-6,7-diyl bis(methylcarbamate);
  (4aR,10aR)-1-propyl-1,2,3,4,4a,5,10,10a-octahydrobenzo[g]quinoline-6,7-diyl bis(ethylcarbamate);
  (4aR,10aR)-1-propyl-1,2,3,4,4a,5,10,10a-octahydrobenzo[g]quinoline-6,7-diyl bis(dimethylcarbamate);
  ((((4aR,10aR)-7-hydroxy-1-propyl-1,2,3,4,4a,5,10,10a-octahydrobenzo[g]-quinolin-6-yl)oxy)carbonyl)glycine;
  ((((4aR,10aR)-6-hydroxy-1-propyl-1,2,3,4,4a,5,10,10a-octahydrobenzo[g]-quinolin-7-yl)oxy)carbonyl)glycine;
  (S)-2-amino-3-(3-(((((4aR,10aR)-7-hydroxy-1-propyl-1,2,3,4,4a,5,10,10a-octahydrobenzo[g]quinolin-6-yl) oxy) carbonyl)amino)phenyl) propanoic acid;
  and pharmaceutically acceptable salts of any of these compounds.

9. The compound according to claim 5, wherein the compound is selected from the group consisting of:
  (4aR,10aR)-1-propyl-1,2,3,4,4a,5,10,10a-octahydrobenzo[g]quinoline-6,7-diyl bis(methylcarbamate);
  (4aR,10aR)-1-propyl-1,2,3,4,4a,5,10,10a-octahydrobenzo[g]quinoline-6,7-diyl bis(ethylcarbamate);
  (4aR,10aR)-1-propyl-1,2,3,4,4a,5,10,10a-octahydrobenzo[g]quinoline-6,7-diyl bis(dimethylcarbamate);
  and pharmaceutically acceptable salts of any of these compounds.

10. A pharmaceutical composition comprising a compound or pharmaceutically acceptable salt thereof according to claim 1, and one or more pharmaceutically acceptable excipients.

11. A method for the treatment of a neurodegenerative disease or disorder, Parkinson's Disease, Huntington's disease, Restless leg syndrome, Alzheimer's disease; a neuropsychiatric disease or disorder, schizophrenia, attention deficit hyperactivity disorder, or drug addiction; which method comprises the administration of a therapeutically effective amount of a compound or pharmaceutically acceptable salt thereof according to claim 1, to a patient in need thereof.

12. The method according to claim 11, wherein said neurodegenerative disease or disorder is Parkinson's Disease.

13. The pharmaceutical composition of claim 10, wherein the compound or pharmaceutically acceptable salt thereof is selected from the group consisting of:
  (4aR,10aR)-1-propyl-1,2,3,4,4a,5,10,10a-octahydrobenzo[g]quinoline-6,7-diyl bis(methylcarbamate);
  (4aR,10aR)-1-propyl-1,2,3,4,4a,5,10,10a-octahydrobenzo[g]quinoline-6,7-diyl bis(ethylcarbamate);
  (4aR,10aR)-1-propyl-1,2,3,4,4a,5,10,10a-octahydrobenzo[g]quinoline-6,7-diyl bis(dimethylcarbamate);
  ((((4aR,10aR)-7-hydroxy-1-propyl-1,2,3,4,4a,5,10,10a-octahydrobenzo[g]-quinolin-6-yl)oxy)carbonyl)glycine;
  ((((4aR,10aR)-6-hydroxy-1-propyl-1,2,3,4,4a,5,10,10a-octahydrobenzo[g]-quinolin-7-yl)oxy)carbonyl)glycine;
  (S)-2-amino-3-(3-(((((4aR,10aR)-7-hydroxy-1-propyl-1,2,3,4,4a,5,10,10a-octahydrobenzo[g]quinolin-6-yl) oxy) carbonyl)amino)phenyl) propanoic acid;
  and pharmaceutically acceptable salts of any of these compounds.

14. The method of claim 11, wherein the compound or pharmaceutically acceptable salt thereof is selected from the group consisting of:
- (4aR,10aR)-1-propyl-1,2,3,4,4a,5,10,10a-octahydrobenzo[g]quinoline-6,7-diyl bis(methylcarbamate);
- (4aR,10aR)-1-propyl-1,2,3,4,4a,5,10,10a-octahydrobenzo[g]quinoline-6,7-diyl bis(ethylcarbamate);
- (4aR,10aR)-1-propyl-1,2,3,4,4a,5,10,10a-octahydrobenzo[g]quinoline-6,7-diyl bis(dimethylcarbamate);
- ((((4aR,10aR)-7-hydroxy-1-propyl-1,2,3,4,4a,5,10,10a-octahydrobenzo[g]-quinolin-6-yl)oxy)carbonyl)glycine;
- ((((4aR,10aR)-6-hydroxy-1-propyl-1,2,3,4,4a,5,10,10a-octahydrobenzo[g]-quinolin-7-yl)oxy)carbonyl)glycine; and
- (S)-2-amino-3-(3-(((((4aR,10aR)-7-hydroxy-1-propyl-1,2,3,4,4a,5,10,10a-octahydrobenzo[g]quinolin-6-yl)oxy) carbonyl)amino)phenyl) propanoic acid;
- and pharmaceutically acceptable salts of any of these compounds.

15. A pharmaceutical composition comprising a compound or pharmaceutically acceptable salt thereof according to claim 5, and one or more pharmaceutically acceptable excipients.

16. A method for the treatment of a neurodegenerative disease or disorder, Parkinson's Disease, Huntington's disease, Restless leg syndrome, Alzheimer's disease; a neuropsychiatric disease or disorder, schizophrenia, attention deficit hyperactivity disorder, or drug addiction; which method comprises the administration of a therapeutically effective amount of a compound or pharmaceutically acceptable salt thereof according to claim 5, to a patient in need thereof.

17. The method according to claim 16, wherein said neurodegenerative disease or disorder is Parkinson's Disease.

18. The pharmaceutical composition according to claim 15, wherein the compound is selected from the group consisting of:
- (4aR,10aR)-1-propyl-1,2,3,4,4a,5,10,10a-octahydrobenzo[g]quinoline-6,7-diyl bis(methylcarbamate);
- (4aR,10aR)-1-propyl-1,2,3,4,4a,5,10,10a-octahydrobenzo[g]quinoline-6,7-diyl bis(ethylcarbamate);
- (4aR,10aR)-1-propyl-1,2,3,4,4a,5,10,10a-octahydrobenzo[g]quinoline-6,7-diyl bis(dimethylcarbamate);
- and pharmaceutically acceptable salts of any of these compounds.

19. The method for the treatment according to claim 16, wherein the compound is selected from the group consisting of:
- (4aR,10aR)-1-propyl-1,2,3,4,4a,5,10,10a-octahydrobenzo[g]quinoline-6,7-diyl bis(methylcarbamate);
- (4aR,10aR)-1-propyl-1,2,3,4,4a,5,10,10a-octahydrobenzo[g]quinoline-6,7-diyl bis(ethylcarbamate);
- (4aR,10aR)-1-propyl-1,2,3,4,4a,5,10,10a-octahydrobenzo[g]quinoline-6,7-diyl bis(dimethylcarbamate);
- and pharmaceutically acceptable salts of any of these compounds.

20. The method according to claim 19, wherein said neurodegenerative disease or disorder is Parkinson's Disease.

21. The compound according to claim 5, wherein the compound is (4aR,10aR)-1-propyl-1,2,3,4,4a,5,10,10a-octahydrobenzo[g]quinoline-6,7-diyl bis(methylcarbamate) or a pharmaceutically acceptable salt thereof.

22. The compound according to claim 5, wherein the compound is (4aR,10aR)-1-propyl-1,2,3,4,4a,5,10,10a-octahydrobenzo[g]quinoline-6,7-diyl bis(ethylcarbamate) or a pharmaceutically acceptable salt thereof.

23. The compound according to claim 5, wherein the compound is (4aR,10aR)-1-propyl-1,2,3,4,4a,5,10,10a-octahydrobenzo[g]quinoline-6,7-diyl bis(dimethylcarbamate) or a pharmaceutically acceptable salt thereof.

24. The compound according to claim 1, wherein R1, R2, R3 and R4 are each individually selected from the group consisting of H and $C_{1-6}$ alkyl.

* * * * *